(12) United States Patent
Powis

(10) Patent No.: US 7,723,375 B2
(45) Date of Patent: May 25, 2010

(54) METABOLITES OF WORTMANNIN ANALOGS AND METHODS OF USING THE SAME

(75) Inventor: Garth Powis, Houston, TX (US)

(73) Assignee: Arizona Board of Regents, acting on behalf of The University of Arizona, Tucson, AZ (US)

( * ) Notice: Subject to any disclaimer, the term of this patent is extended or adjusted under 35 U.S.C. 154(b) by 222 days.

(21) Appl. No.: 11/618,036

(22) Filed: Dec. 29, 2006

(65) Prior Publication Data

US 2007/0191466 A1 Aug. 16, 2007
US 2010/0063129 A9 Mar. 11, 2010

Related U.S. Application Data

(63) Continuation-in-part of application No. 11/178,553, filed on Jul. 11, 2005, now Pat. No. 7,446,124.

(60) Provisional application No. 60/755,477, filed on Dec. 30, 2005, provisional application No. 60/586,687, filed on Jul. 9, 2004.

(51) Int. Cl.
  *A61K 31/352* (2006.01)
  *A61K 31/407* (2006.01)
  *C07D 311/78* (2006.01)
  *C07D 405/02* (2006.01)

(52) U.S. Cl. ............... 514/422; 514/453; 548/525; 549/383

(58) Field of Classification Search ............ 514/422, 514/453; 548/525; 549/383
See application file for complete search history.

(56) References Cited

U.S. PATENT DOCUMENTS

| | | | |
|---|---|---|---|
| 5,001,064 | A | 3/1991 | Deuel |
| 5,480,906 | A | 1/1996 | Creemer et al. |
| 5,602,278 | A | 2/1997 | Kirkpatrick |
| 6,703,414 | B2 | 3/2004 | Powis et al. |
| 7,081,475 | B2 | 7/2006 | Powis et al. |
| 2006/0063824 | A1 | 3/2006 | Kirkpatrick et al. |
| 2006/0128793 | A1 | 6/2006 | Zask et al. |

FOREIGN PATENT DOCUMENTS

| | | |
|---|---|---|
| EP | 0658343 A1 | 6/1995 |
| GB | 2302021 | 1/1997 |
| WO | WO 90/01969 A1 | 8/1989 |
| WO | WO 03/024183 A3 | 3/2003 |
| WO | WO 2006/044453 A1 | 4/2006 |
| WO | WO 2007/008200 A1 | 1/2007 |

OTHER PUBLICATIONS

Haefliger et al., Isolierung und Strukturaufklarung von 11-Desacetoxy-wortmannin, 1973, Helvetica Chimica Acta 56(8 No. 300-301):2901-2904, (Abstract).

Haefliger et al., Selektive Funktionalisierung von Wortmannin mit Hilfe einer Furanring-Maskierung, 1975, Helvetica Chimica Acta 58(6 No. 179-180):1620-1628, (Abstract).
Ihle et al., Molecular pharmacology and antitumor activity of PX-866, a novel inhibitor of phosphoinositide-3-kinase signaling. 2004, Mol. Cancer Ther. 3(7):1-10.
Wipf et al., Synthesis and biological evaluation of synthetic vindins derived from C(20)-heteroalkylation of the steroidal PI-3 kinase inhibitor wortmannin, 2004, Org. Biomol. Chem. 2:1911-1920.
Langer, New Methods of Drug Delivery, 1990. Science 249:1527-1533.
Mathiowitz et al., Photochemical Rupture of Microcapsules: A Model System, 1981, J. App. Poly. Sci. 26:809-822.
Breivis et al., Faranoxi-A New Antitumor Agent, 1996, J. Chemotherapy 8(1):67-69.
Zalgevicience et al., Embryotoxicity and Teratogenicity of Some Derivatives of Chloroethylaminophenylacetic Acid, 1996, Pathology Oncology Research 4(1):27-29.
Berridge et al. Inositol trisphosphate, a novel second messenger in cellular signal transduction, 1984, Nature 312.315-321.
Nishizuka, Turnover of Inositol Phospholipids and Signal Transduction, 1984, Science 255:1365-1370.
Shibasaki et al., Two Types of Phosphatidylinositol 3-Kinase from Bovine Thymus, 1991, J. Biol. Chem. 266(13):8108-8114.
Courtneidge et al., An 81 kd Protein Complesed with Middle T Antigen and pp60$^{c-src}$: A Possible Phosphatidylinisitol Kinase, 1987, Cell 50:1031-1037.
Kaplan et al., Common Elements in Growth Factor Stimulation and Oncogenic Transformation 85 kd Phosphorprotein and Phosphatidylinositol Kinase Activity 1987, Cell 50:1021-1029.
Whitman et al., Type I phosphatidylinositol kinase makes a novel inositol phospholipid phosphatidylinositol-3-phosphate, 1988, Nature 332:644-646.
Auger et al. PDGF-Dependent Tyrosine Phosphorylation Stimulates Productidn of Novel Polyphosphoinositides in Intact Cells, 1989, Cell 57:167-175.
Traynor-Kaplan et al., An inositol tetrakisphosphate-containing phospholipid in activated neutrophils, 1988; Nature 334:353-356.
Mitchell et al., Thrombin-stimulated immunoprecipitation of phosphatidylinoeitol 3-kinase from human platelets. 1990, Proc. Natl. Acad. Sci. 67:9396-9400.
Vlahos et al., Signal transduction in neutrophil activation: Phosphatidylinositol 3-kinase is stimulated without: tyrosine. phosphorylation, 1992, FEBS Letters 309(3):242-248.
Cantley et al., Oncogenes and Signal Transduction, 1991 Cell 64:281-302.
Margolis, Proteins with SH2 Domains: Transducers in the Tyrosine Kinase Signaling Pathway; 1992, Cell Growth Differ. 3:73-80.
Matter et al., The Inhibition of Phosphatidylinositol 3-Kinase by Quercetin and Analogs, 1992, Biochem, Biophys. Res. Commun. 186(2):624-631.
Nakanishi et al., Wortmannin, a Microbial Product Inhibitor of Myosin Light Chain Kinase, 1992, J. Biol. Chem. 267(4):2157-2163.

(Continued)

*Primary Examiner*—Taofiq A Solola
(74) *Attorney, Agent, or Firm*—Pepper Hamilton LLP

(57) ABSTRACT

Novel metabolites of wortmannin and wortmannin analogs and their use in inhibiting PI-3 kinase activity in mammals and the treatment and prevention of cancer or tumor formation in a subject are described herein.

6 Claims, 14 Drawing Sheets

OTHER PUBLICATIONS

Abbas et al., Isolation and Purification of a Hemorrhagic Factor (Wortmannin) from *Fusarium oxysporum* (N17B), 1988, Appl. Environ, Microbial. 54(5):1267-1274.

Baggiolini et al., Inhibition of the Phagocytosis-Induced Respiratory Burst by the Fungal Metabolite Wortmannin and Some Analogues, 1987, Exp. Cell Res. 169:408-418.

MacMillan et al., Fungal Products, Part II Structure and Stereochemistry of the Acid $C_{18}H_{16}O_5$, a Degradation Product of Wortimannin 1972, J. Chem. Soc. Perkin I:2892-2898.

Folch et al., A Simple Method for the Isolation and Purification of Total Lipides from Animal Tissues, 1957 J. Biol. Chem. 226:497-509.

Clarke et al., Alkaline O→N-transacylation, 1981, Biochem. J. 195:301-306.

Auger et al, Methods in Inositide Research, pp. 159-166, Irvine ed., Raven Press, Ltd, New York. 1990.

Norman et al., Studies on the Mechanism of Phosphatidylinositol 3-Kinase Inhibiton by Wortmannin and Related Analogs 1996, J. Med. Chem. 39:1106-1111.

Kohn Current Trends in the Development of Synthetic Materials for Medical Applications. Oct. 1990, Pharmaceutical Technology, pp. 32-41.

Ciardiello et al. Epidermal Growth Factor Receptor Tyrosine Kinase Inhibitors in Late Stage Clinical. Trials, 2003, Expert Opinion on Emerging Drugs, 8(2):501-514.

Sorensen et al. Paclitaxel, Gemcitabine, and Cisplatin in Non-resectable Non-small-cell Lung Cancer, 1999, Annals of Oncology, 10(9);1043-1049.

Kirkpatrick et al. Antitumor Activity, Pharmacodynamics and Toxicity of PX-866 a Novel Inhibitor of Phosphoinositide-3-kinase, 2004, European Journal of Cancer, 2(8): 77.

Ihle et al. Molecular Pharmacology and Antitumor Activity of PX-866, a Novel Inhibitor of Phosphoinositide~3~kinase Signaling, 2004, Molecular Cancer Therapeutics, 3(7):763-772.

METABOLITES OF WORTMANNIN ANALOGS AND METHODS OF USING THE SAME

CROSS-REFERENCE TO RELATED APPLICATIONS

This application is a continuation-in-part of U.S. patent application Ser. No. 11/178,553 filed Jul. 11, 2005, now U.S. Pat. No. 7,446,124 issued Mar. 23, 2006 and claims priority to U.S. Provisional Application Ser. No. 60/755,477 filed Dec. 30, 2005, both applications being incorporated herein by reference in their entirety.

STATEMENT REGARDING FEDERALLY FUNDED RESEARCH

The United States Government may have certain interests to this application as a Federal Research Sponsor under NIH/NIG Grant Nos. U19 CA-52995.

THE NAMES OF THE PARTIES TO A JOINT VENTURE AGREEMENT

Not Applicable

INCORPORATION-BY-REFERENCE TO MATERIAL ON DISK

Not Applicable

BACKGROUND

The present disclosure relates to wortmannin analogs and metabolites thereof, and has application to methods of using these derivatives to inhibit phosphotidylinositol-3-kinase (PI-3-kinase) activity and to treat certain malignant tumors.

The PI-3 kinases are a family of related enzymes that are capable of phosphorylating the 3 position hydroxyl group of the inositol ring of phosphatidylinositol. They are linked to a diverse list of cellular functions, including cell growth, proliferation, differentiation, motility, survival and intracellular trafficking. Many of these functions relate to the ability of the PI-3 kinases to activate the protein kinase B (Akt). Genetic and pharmacological inactivation of the p110δ isoform of the PI-3 kinase has revealed this enzyme to be important for the function of T cells, B cell, mast cells and neutrophils. Hence, p110δ is considered to be a promising target for drugs that aim to prevent or treat inflammation and autoimmunity and transplant rejection. Recent evidence has shown that the gene encoding the p110α isoform of the PI-3 kinase is mutated in a range of human cancers. For example, mutation of p110α which leads to over-expression of the kinase is found in human lung cancer. PI-3 kinase activity is also found to be elevated in ovarian, head and neck, urinary tract, colon and cervical cancers. Further, a phosphate $(PtdIns(3,4,5)P_3)$ which antagonizes PI-3 kinase activity is absent or mutated in a variety of human cancers, including advanced prostate, endometrial, renal, glial, melanoma, and small cell lung cancers. Thus, inhibition of PI-3 kinase activity may provide a potential target for treatment of certain human cancers.

Wortmannin is a naturally occurring compound isolated from culture broths of the fungus *Penicillium wortmannin* that has the basic structure shown in U.S. Pat. No. 5,480,906, which is incorporated herein by reference. Wortmannin irreversibly inhibits PI-3-kinase through covalent interaction with a specific lysine on the kinase: $Lys^{802}$ of the ATP binding pocket of the catalytic site of the p110α isoform or $Lys^{883}$ of the p110δ isoform. Most isoforms of PI-3 kinase, such as p110α, p110β, p110δ and p110γ for example, are inhibited equally by wortmannin. Wortmannin demonstrates liver and hematologic toxicity, however, and is a biologically unstable molecule. Samples stored as aqueous solutions at either 37° C. or 0° C. at neutral pH are subject to decomposition by hydrolytic opening of the furan ring. It has been shown that the electrophilicity of the furan ring is central to the inhibitory activity of wortmannin. The irreversible inhibition of PI-3-kinase occurs by formation of an enamine following the attack of the active lysine of the kinase on the furan ring at position (C(20) of wortmannin. Thus, decomposition of wortmannin may interfere with its inhibitory activity on PI-3 kinases.

Analogs of wortmannin that display improved biological stability and reduced systemic toxicity may provide improved treatment for cancer and act as anti-tumor agents. Accordingly, what is needed are analogs of wortmannin and metabolites thereof that display increased biological stability and reduced toxicity.

SUMMARY

The present disclosure relates to metabolites of wortmannin and metabolites of wortmannin analogs and their use in inhibiting PI-3 kinase, treating and preventing tumor growth, and treating cancer.

An embodiment of the disclosure provides for a compound of structure 10:

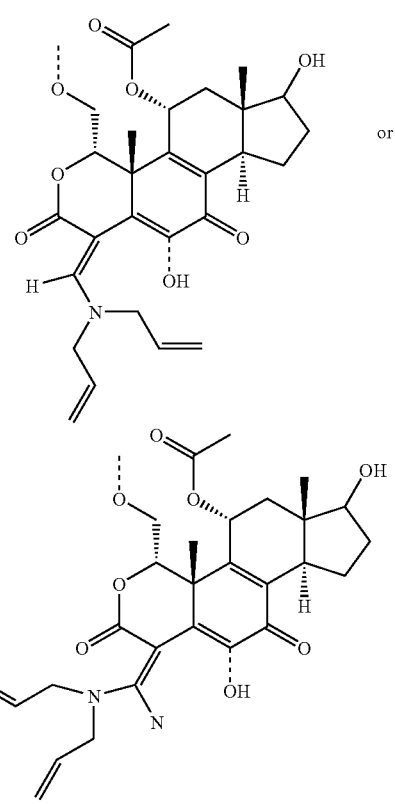

An additional embodiment of the disclosure provides for a compound of structure 9:

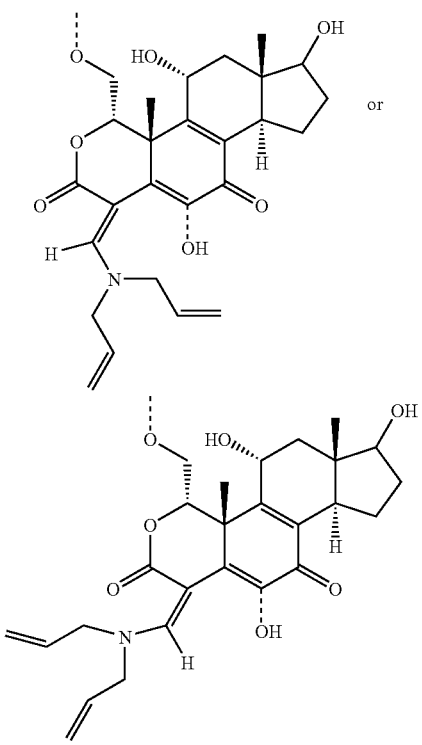

Yet another embodiment of the disclosure provides for a compound of structure 7:

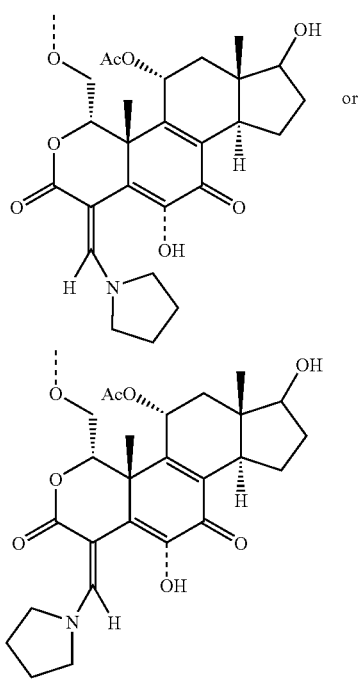

Another embodiment of the disclosure provides a method of inhibiting PI-3 kinase activity in mammals comprising administering to a mammal an effective amount of the compound of structure 10. An additional embodiment of the disclosure provides for method of inhibiting PI-3 kinase activity in mammals comprising administering to a mammal an effective amount of the compound of structure 9. An additional embodiment of the disclosure provides for method of inhibiting PI-3 kinase activity in mammals comprising administering to a mammal an effective amount of the compound of structure 7.

Another embodiment of the disclosure provides a method of inhibiting PI-3 kinase activity in a cell comprising contacting the cell with the compound of structure 10, whereby the compound inhibits PI-3 kinase. An additional embodiment of the disclosure provides for a method of inhibiting PI-3 kinase activity in a cell comprising contacting the cell with the compound of structure 9, whereby the compound inhibits PI-3 kinase. An additional embodiment of the disclosure provides for a method of inhibiting PI-3 kinase activity in a cell comprising contacting the cell with the compound of structure 7, whereby the compound inhibits PI-3 kinase.

Since PI-3 kinase activity may be a factor in certain types of cancers, the present disclosure also provides for use of the compounds as anti-tumor agents, anti-cancer agents, and for pharmaceutical compositions useful for the treatment of such tumors or cancers. As such, an additional embodiment of the disclosure provides for a method of treating cancer comprising administering to a subject therapeutically effective amount of the compound of structure 10. The cancer treated by the compound of structure 10 may be colon cancer. Another embodiment of the disclosure provides for a method of treating cancer comprising administering to a subject a therapeutically effective amount of the compound of structure 9. The cancer treated by the compound of structure 9 may be colon cancer. Another embodiment of the disclosure provides for a method of treating cancer comprising administering to a subject a therapeutically effective amount of the compound of structure 7. The cancer treated by the compound of structure 7 may be colon cancer.

Embodiments of the disclosure also provide for a pharmaceutical composition comprising an effective amount of the compound of structure 10, and a pharmaceutically acceptable carrier, diluent, or excipient thereof. Additional embodiments of the disclosure provide for a pharmaceutical composition comprising an effective amount of the compound of structure 9, and a pharmaceutically acceptable carrier, diluent, or excipient thereof. Additional embodiments of the disclosure provide of a pharmaceutical composition comprising an effective amount of the compound of structure 7, and a pharmaceutically acceptable carrier, diluent, or excipient thereof.

Embodiments of the disclosure also provide for a method of treating tumor cell proliferation of tumor cell growth comprising administering to a subject an effective amount of a compound of structure 10. An additional embodiment of the disclosure provides a method of treating tumor cell proliferation or tumor cell growth comprising administering to a subject an effective amount of a compound of structure 9. Yet another embodiment of the disclosure provides a method of treating tumor cell proliferation or tumor cell growth comprising administering to a subject an effective amount of a compound of structure 7.

BRIEF DESCRIPTION OF THE DRAWINGS

For a better understanding of the disclosure and to show how the same may be carried into effect, reference will now be made to the accompanying drawings. It is stressed that the particulars shown are by way of example only and for purposes of illustrative discussion of the preferred embodiments of the present disclosure only, and are presented in the cause of providing what is believed to be the most useful and readily understood description of the principles and conceptual aspects of the invention. In this regard, no attempt is made to show experimental details of the invention in more detail than is necessary for a fundamental understanding of the invention, the description taken with the drawings making apparent to those skilled in the art how the several forms of the invention may be embodied in practice. In the accompanying drawings.

DETAILED DESCRIPTION

Figure 1:
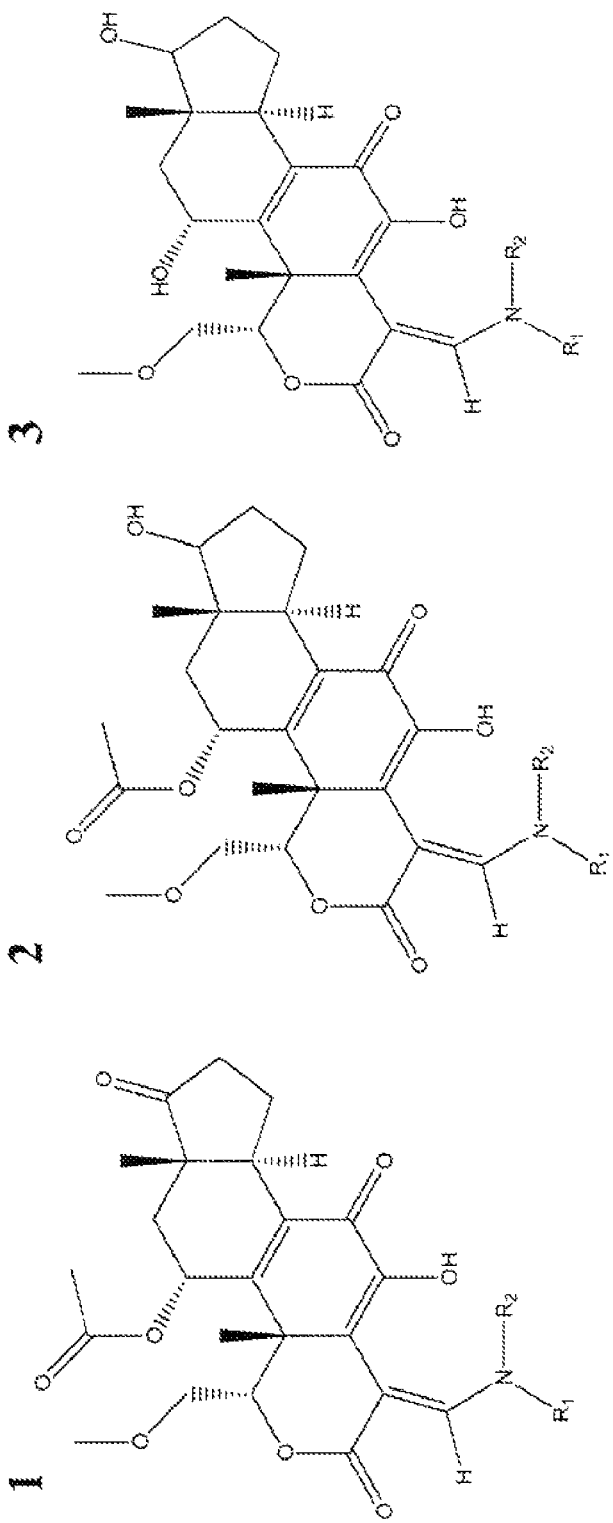
FIG. 1 illustrates formulas for exemplary wortmannin analog and metabolite structures in accord with the present disclosure.

Before the present compositions and methods are described, it is to be understood that this invention is not limited to the particular processes, compositions, or methodologies described, as these may vary. It is also to be understood that the terminology used in the description is for the purpose of describing the particular versions or embodiments only, and is not intended to limit the scope of the present invention which will be limited only by the appended claims.

It must also be noted that as used herein and in the appended claims, the singular forms "a", "an", and "the" include plural reference unless the context clearly dictates otherwise. Thus, for example, reference to a "cell" is a reference to one or more cells and equivalents thereof known to those skilled in the art, and so forth. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference in their entirety. Nothing herein is to be construed as an admission that the invention is not entitled to antedate such disclosure by virtue of prior invention.

As used herein, the term "about" means plus or minus 10% of the numerical value of the number with which it is being used. Therefore, about 50% means in the range of 45%-55%. "Optional" or "optionally" may be taken to mean that the subsequently described structure, event or circumstance may or may not occur, and that the description includes instances where the events occurs and instances where it does not.

"Administering" when used in conjunction with a therapeutic means to administer a therapeutic systemically or locally, as directly into or onto a target tissue, or to administer a therapeutic to a patient whereby the therapeutic positively impacts the tissue to which it is targeted. Thus, as used herein, the term "administering", when used in conjunction with a wortmannin analog or metabolite thereof, can include, but is not limited to, providing a wortmannin analog or metabolite thereof into or onto the target tissue; providing a wortmannin analog or metabolite thereof systemically to a patient by, e.g., intravenous injection whereby the therapeutic reaches the target tissue or cells. "Administering" a composition may be accomplished by injection, topical administration, and oral administration or by other methods alone or in combination with other known techniques. Such combination techniques include heating, radiation and ultrasound.

The term "animal" as used herein includes, but is not limited to, humans and non-human vertebrates such as wild, domestic and farm animals. The terms "patient" and "subject" are interchangeable and may be taken to mean any living organism which may be treated with compounds of the present disclosure. As such, the terms "patient" and "subject" may include, but are not limited to, any non-human mammal, any primate or a human.

The term "inhibiting" includes the administration of a compound of the present disclosure to prevent the onset of symptoms, alleviate symptoms, or eliminate the disease, condition or disorder.

By "pharmaceutically acceptable", it is meant the carrier, diluent or excipient must be compatible with the other ingredients of the formulation and not deleterious to the recipient thereof.

The term "pharmaceutical composition" shall mean a composition comprising at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

As used herein, the term "therapeutic" means an agent utilized to treat, combat, ameliorate, prevent or improve an unwanted condition or disease of a patient. In part, embodiments of the present disclosure are directed to the treatment of cancer or the decrease in proliferation of cells.

A "therapeutically effective amount" or "effective amount" as used herein refers to the amount of active compound or pharmaceutical agent that elicits a biological or medicinal response in a tissue, system, animal, individual or human that is being sought by a researcher, veterinarian, medical doctor or other clinician, which includes one or more of the following (1) preventing the disease; for example, preventing a disease, condition or disorder in an individual that may be predisposed to the disease, condition or disorder but does not yet experience or display the pathology or symptomatology of the disease (2) inhibiting the disease; for example, inhibiting a disease, condition or disorder in an individual that is experiencing or displaying the pathology or symptomatology of the disease, condition or disorder (i.e., arresting further development of the pathology and/or symptomatology), and (3) ameliorating the disease; for example, ameliorating a disease; condition or disorder in an individual that is experiencing or displaying the pathology or symptomatology of the disease, condition or disorder (i.e., reversing the pathology and/or symptomatology). As such, a non-limiting example of a "therapeutically effective amount" or "effective amount" of a composition of the present disclosure may be used to inhibit, block, or reverse the activation, migration, or proliferation of cells or to effectively treat cancer or ameliorate the symptoms of cancer.

The activity contemplated by the present methods includes both medical therapeutic and/or prophylactic treatment, as appropriate. The specific dose of a compound administered according to this invention to obtain therapeutic and/or prophylactic effects will, of course, be determined by the particular circumstances surrounding the case, including, for example, the compound administered, the route of administration, and the condition being treated. The compounds are effective over a wide dosage range and, for example, dosages per day will normally fall within the range of from 0.001 to 100 mg/kg, more usually in the range of from 0.01 to 1 mg/kg. However, it will be understood that the effective amount administered will be determined by the physician in light of the relevant circumstances including the condition to be treated, the choice of compound to be administered, and the chosen route of administration, and therefore the above dosage ranges are not intended to limit the scope of the invention in any way. A therapeutically effective amount of compound of this invention is typically an amount such that when it is administered in a physiologically tolerable excipient composition, it is sufficient to achieve an effective systemic concentration or local concentration in the tissue.

The terms "treat," "treated," or "treating" as used herein refers to both therapeutic treatment and prophylactic or preventative measures, wherein the object is to prevent or slow (lessen) an undesired physiological condition, disorder or disease, or to obtain beneficial or desired clinical results. For the purposes of this invention, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment.

Embodiments of the present invention provide novel metabolites of wortmannin and metabolites of wortmannin analogs as well as methods of inhibiting cancer in a subject comprising administering to a subject a pharmaceutically effective amount of such wortmannin analogs and metabolites of wortmannin and wortmannin analogs.

Further embodiments of the present invention also provide for methods of inhibiting PI-3-kinase activity in mammals by administration of an effective amount of one of the compounds of this disclosure. Since PI-3-kinase activity is a factor in certain types of cancer, the invention also provides for use of the compounds as anti-cancer (anti-tumor) agents, and for pharmaceutical compositions that include the compounds in combination with pharmaceutically acceptable carriers, excipients or diluents.

FIG. 1 illustrates formulas for exemplary wortmannin analogs and metabolites thereof that may be useful in accordance with the present invention. Formulation of wortmannin analogs is well known in the art, as is the fermentation process. One ordinary skilled in the art may use common synthetic and synthesis schemes to formulate compounds of formula 1, 2 or 3, as shown in FIG. 1. Thus, an embodiment of the disclosure provides for compounds of formula 1, as shown:

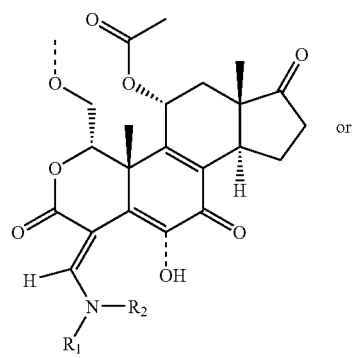

Formula 1

-continued

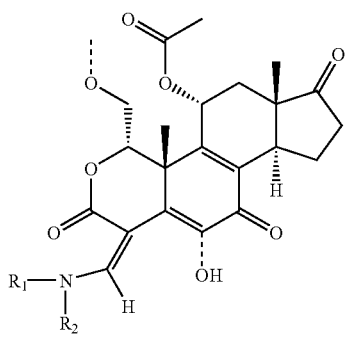

wherein R1 and R2 are unsaturated alkyl, saturated alky, non-linear alkyl, branched alkyl, substituted alkyl or cyclic alkyl.

An additional embodiment of the disclosure provides for compounds of formula 2, as shown:

Formula 2

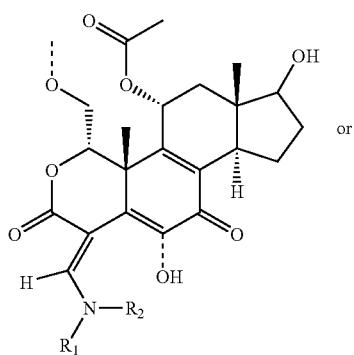

or

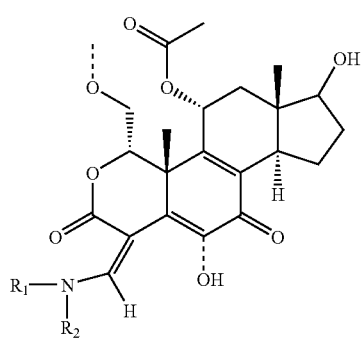

wherein R1 and R2 are unsaturated alkyl, saturated alkyl, non-linear alkyl, branched alkyl, substituted alkyl or cyclic alkyl.

Yet another embodiment of the disclosure provides for compounds of formula 3, as shown:

Formula 3

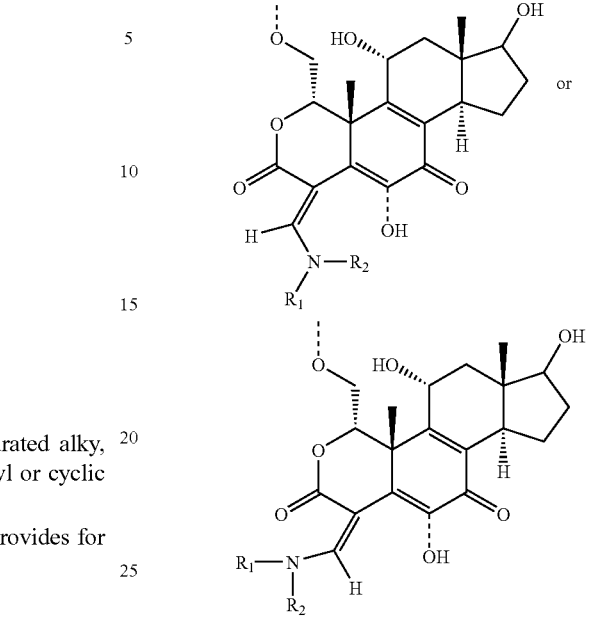

wherein R1 and R2 are unsaturated alkyl, saturated alkyl, non-linear alkyl, branched alkyl, substituted alkyl or cyclic alkyl.

Figure 2:
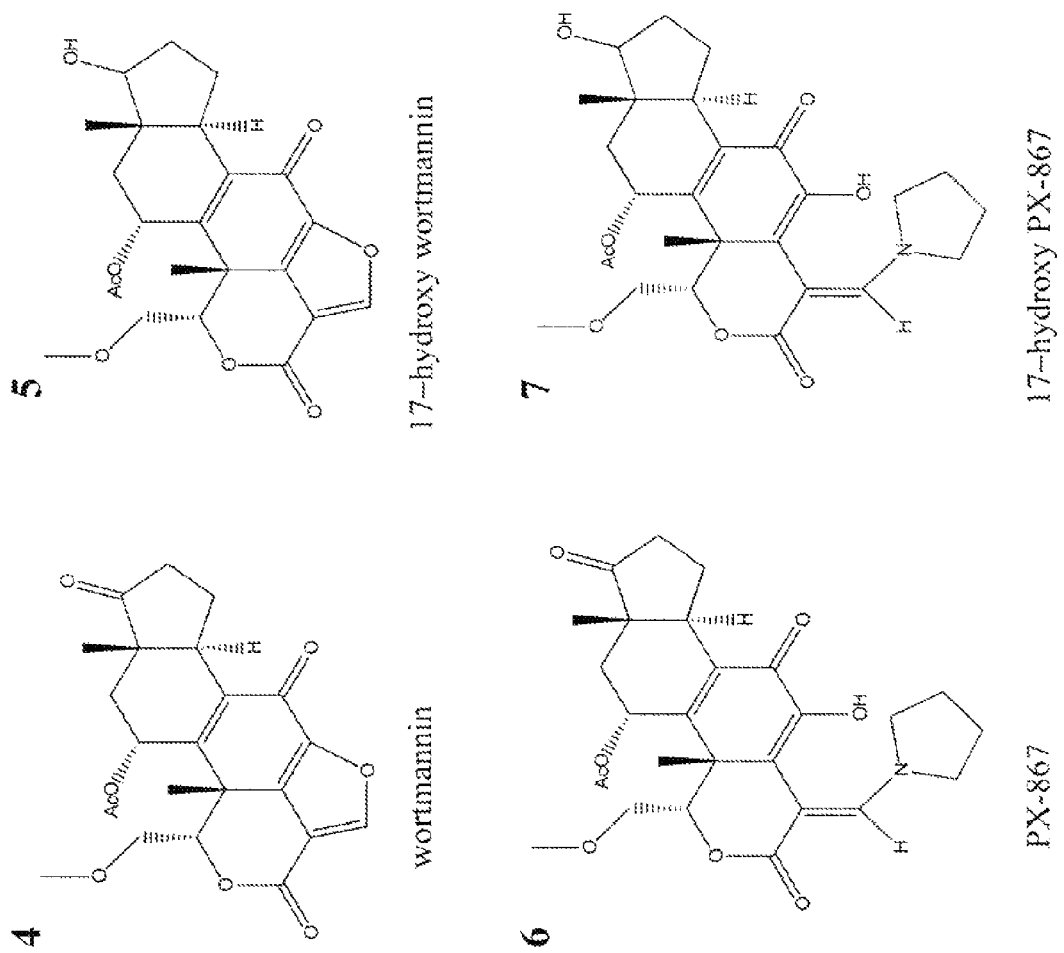
FIG. 2 illustrates formulas for exemplary wortmannin analog and metabolic structures in accord with the present disclosure.

In a preferred embodiment, compounds of the present disclosure have a chemical structure corresponding to a compound selected from the group consisting of the compounds represented by structures 4-7, as shown in FIG. 2.

Structure 4

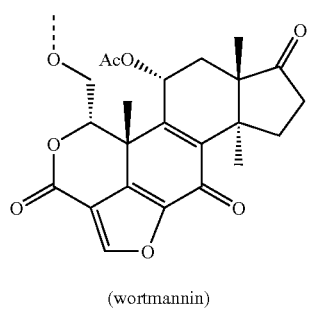

(wortmannin)

Structure 5

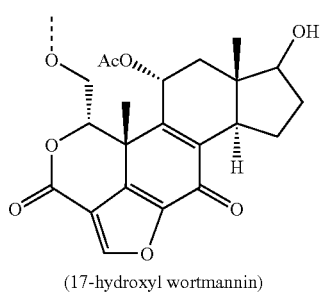

(17-hydroxyl wortmannin)

Structure 6

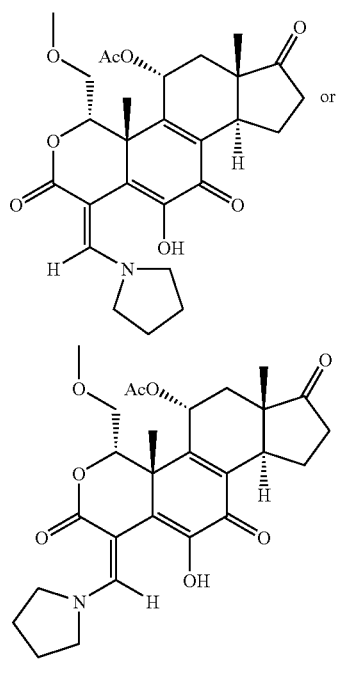

(PX-867)

Structure 7

(17-hydroxyl PX-867)

Structure 8

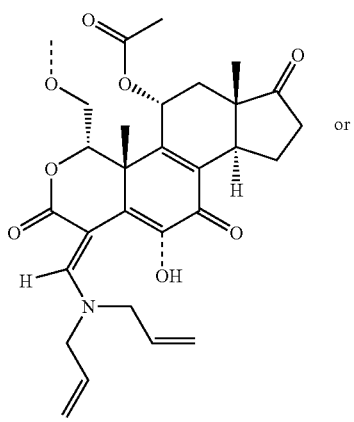

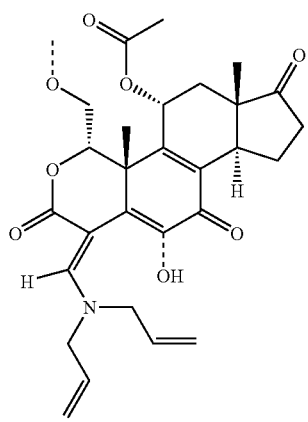

(PX-866)

Structure 9

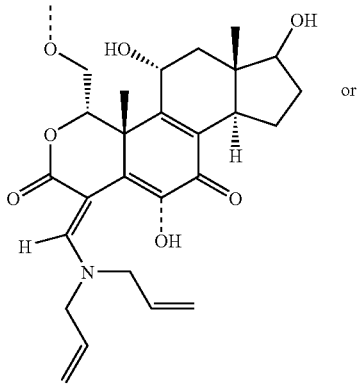

More preferably, compounds of the present disclosure have a chemical structure represented by structures 5 to 7.

Figure 3:
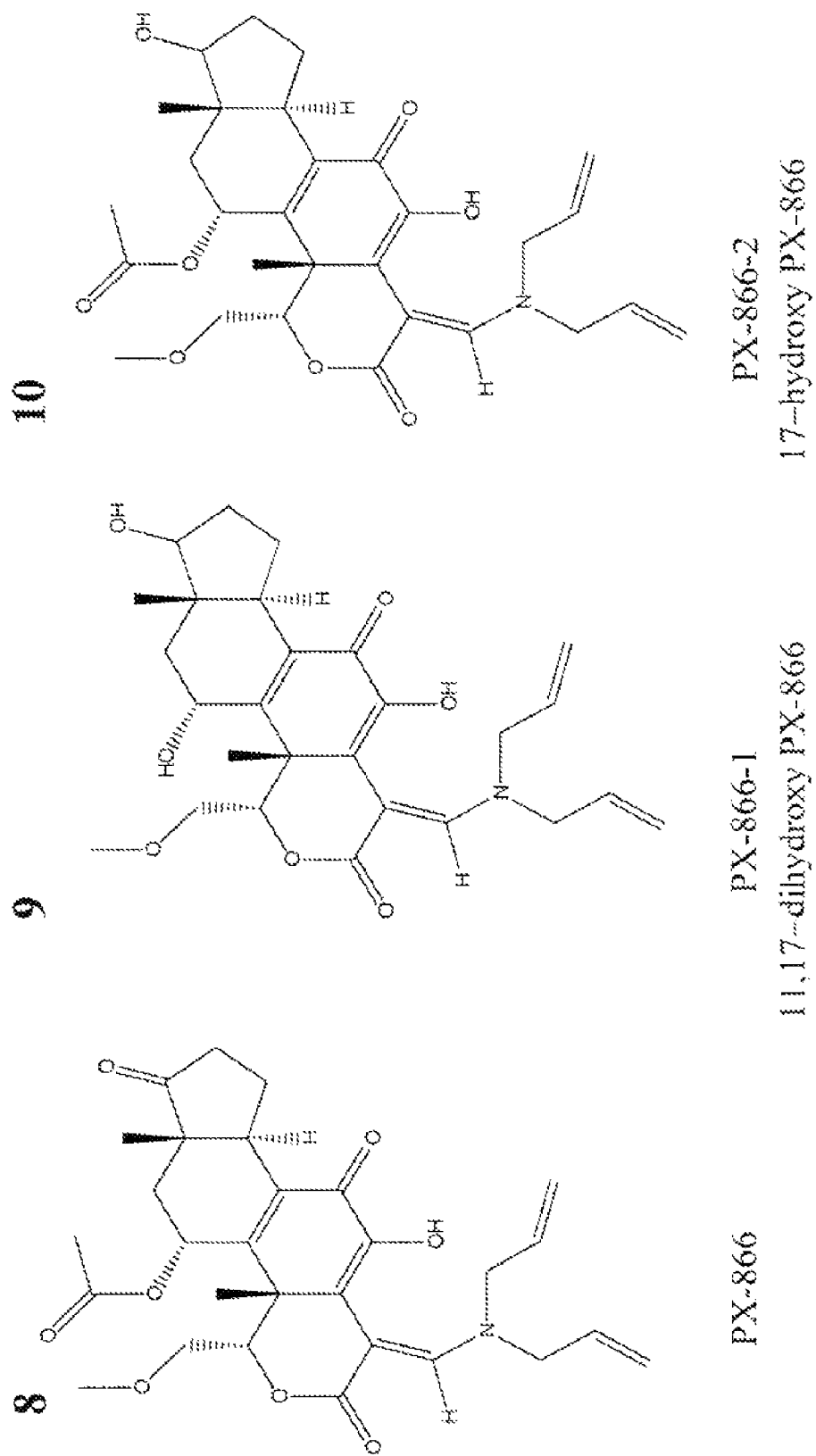
FIG. 3 illustrates formulas for exemplary wortmannin analog and metabolite structures in accord with the present disclosure.

In a more preferred embodiment, compounds of the present disclosure have a chemical structure corresponding to a compound selected from the group consisting of the compounds represented by structures 8-10, as shown in FIG. 3

-continued

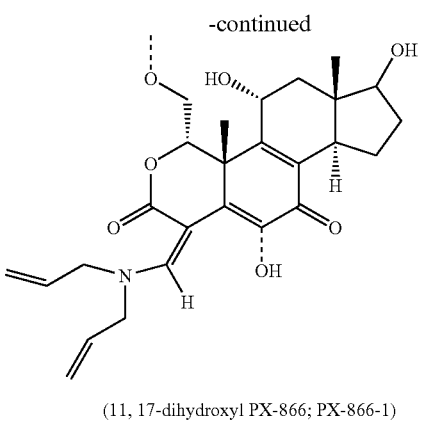

(11, 17-dihydroxyl PX-866; PX-866-1)

Structure 10

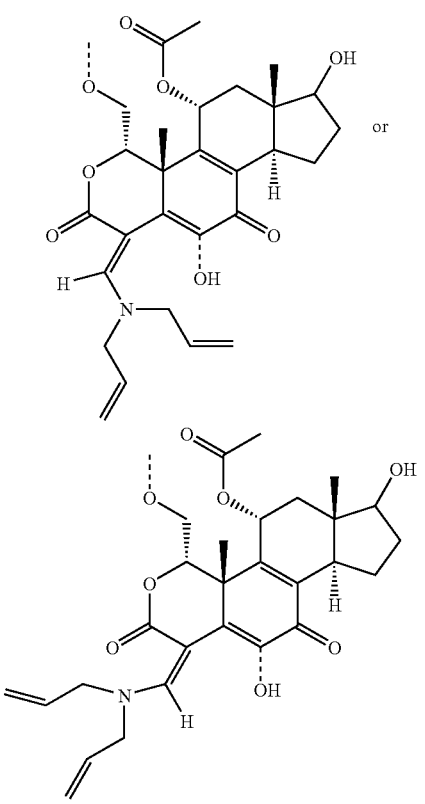

or (17-hydroxyl PX-866; PX-866-2)

More preferably, compounds of the present disclosure have a chemical structure represented by structures 9 and 10.

Exemplary synthesis schemes for PX-866 (structure 8 of FIG. 3) may be found in Example 1; PX-867 (structure 6 of FIG. 12) may be found in Examples 2 and 3; 17-hydroxyl wortmannin (structure 5 in FIG. 2) and 17-hydroxyl PX-867 (structure 7 in FIG. 2) may be found in Example 3.

As employed herein, "alkyl" refers to hydrocarbon radicals having from 1 up to 20 carbon atoms, preferably from 2 up to 10 carbon atoms. The term "unsaturated alkyl" may be taken to indicated that the carbon structure contains double or triple bonds, while "saturated alkyl" is used to indicate that the carbon structure contains the maximum amount of hydrogens possible: i.e., no double bonds or, in a hydrocarbon chain, every carbon atom is attached to two hydrogen atoms.

The term "substituted alkyl" comprises alkyl groups further bearing one or more substituents selected from hdyroxy, alkyl (of a lower alkyl group), mercapto (of a lower alkyl group), cycloalkyl, substituted cycloalkyl, heterocyclic, substituted heterocyclic, aryl, substituted aryl, heteroaryl, substituted heteroaryl, aryloxy, substituted aryloxy, halogen, trifluorometyl, cyano, nitro, nitrosothiol (—SNO), nitrate (i.e., nitrous acid ester), nitrone, nitrite (i.e., nitric acid ester), nitroglyceryl, S-nitrosocysteinyl, S-nitrosoglutathionyl, oxime, N-hydroxylguanidinyl, amino, amido, —C(O)H, acyl, oxyacyl, carboxyl, carbamate, sulfonyl, sulfinyl, sulfonamide, sulfuryl, and the like.

As employed herein, "cyclic alkyl" refers to cyclic ring-containing groups containing in the range of about 3 up to 8 carbon atoms, and "substituted cyclic alkyl" refers to cyclic alkyl groups further bearing one or more substituents as set forth above.

The biosynthetic production of wortmannin is well known in the art and the analogs are synthesized from wortmannin. U.S. Pat. No. 5,480,906, which is incorporated herein by reference in its entirety, describes typical synthetic schemes. In general, wortmannin is produced by the fermentation of any one of a number of microorganisms such as *Talaromyces wortmannin, Penicillium wortmannin, Myrothecium roridium* and *Fusarium*. Following fermentation, wortmannin is extracted and purified via known methods. Preferably, wortmannin is microbially synthesized and isolated in substantially pure form from a fermentation culture; one such fermentation culture is identified as A24603.1.

The strains are cultured under submerged aerobic conditions in a suitable culture medium until a recoverable amount of wortmannin is produced. Wortmannin can be recovered using various isolation and purification procedures understood in the art.

The medium used to grow the culture can be any one of a number of media. For economy in production, optimal yield, and ease of product isolation, however, preferred carbon sources in large-scale fermentation are glucose and soluble starch such as corn starch. Maltose, ribose, xylose, fructose, galactose, mannose, mannitol, potato dextrin, methyl oleate, oils such as soybean oil and the like can also be used.

Preferred nitrogen sources are enzyme-hydrolyzed casein and cottonseed flour, although pepsinized milk, digested soybean meal, fish meal, corn steep liquor, yeast extract, acid-hydrolyzed casein, beef extract and the like can also be used.

Among the nutrient inorganic salts that can be incorporated in the culture media are the customary soluble salts capable of yielding calcium, magnesium, sodium, ammonium, chloride, carbonate, sulfate, nitrate, zinc, and like ions. Essential trace elements necessary for the growth and development of the organism also should be included in the culture medium. Such trace elements commonly occur as impurities in other substituents of the medium in amounts sufficient to meet the growth requirements of the organism.

For production of substantial quantities of wortmannin, submerged aerobic fermentation in stirred bioreactors is preferred. Small quantities of wortmannin may be obtained by shake-flask culture. Because of the time-lag in production commonly associated with inoculation of large bioreactors with the spore form of the organism, it is preferable to use vegetative inoculum. The vegetative inoculum is prepared by inoculating a small volume of culture medium with the spore form or mycelial fragments of the organism to obtain a fresh, actively growing culture of the organism. The vegetative inoculum medium can be the same as that used for larger fermentations, but other media are also suitable.

Following its production, wortmannin can be recovered from the fermentation medium by methods used in the art. The wortmannin produced during fermentation of the A24603.1 organism, for example, occurs mainly in the broth.

Typically, wortmannin can be recovered from the biomass by a variety of techniques. A preferred technique involves filtering whole fermentation broth with a ceramic filter. The filtrate is eluted with an organic solvent such as ethyl acetate and concentrated. The concentrate is suspended in alcohol until crystallization occurs and the solution is filtered, washed and dried. For confirmation, the crystalline material is dissolved in an organic solvent and chromatographed on a reverse-phase silica gel absorbent ($C_8$ or $C_{18}$). Fractions are eluted in an organic-aqueous buffer such as 60% acetonitrile.

Wortmannin may be further manipulated to arrive at the compounds of the present invention. Although the synthesis of particular analogs of wortmannin are illustrated below, other synthetic schemes common in the art will allow one of ordinarily skilled in the art to synthesize compounds in accordance with the present invention, and the synthetic schemes set forth herein should, in no way, be considered limiting.

For therapeutic treatment of the specified indications, metabolites of wortmannin or metabolites of wortmannin analogs of formulas 1-3 as shown in FIG. 1 and structures 4-10 as shown in FIGS. 2-3 may be administered as such, or can be compounded and formulated into pharmaceutical compositions in unit dosage form for parenteral, transdermal, rectal, nasal, local intravenous administration, or, preferably, oral administration. Such pharmaceutical compositions are prepared in a manner well known in the art and comprise at least one active compound selected from the group consisting of those wortmannin analogs or metabolites of wortmannin analogs of formulas 1-3 as shown in FIG. 1 and structures 4-10 as shown in FIGS. 2-3 associated with a pharmaceutically carrier. The term "active compound", as used throughout this specification, refers to at least one compound selected from compounds of the formulas 1-3 as shown in FIG. 1 and structures 4-10 as shown in FIGS. 2-3 or pharmaceutically acceptable salts thereof.

Thus, an embodiment of the disclosure provides for a pharmaceutical composition comprising an effective amount of the compound of formula 2 or 3, as shown in FIG. 1, and a pharmaceutically acceptable carrier, diluent, or excipient thereof. A preferred embodiment of the disclosure provides for a pharmaceutical composition comprising an effective amount of the compound of structure 5 or 7, as shown in FIG. 2, and a pharmaceutically acceptable carrier, diluent, or excipient thereof. A more preferred embodiment of the disclosure provides for a pharmaceutical composition comprising an effective amount of the compound of structure 9 or 10, as shown in FIG. 3, and a pharmaceutically acceptable carrier, diluent, or excipient thereof.

In such a composition, the active compound is known as the "active ingredient". In making the compositions, the active ingredient will usually be mixed with a carrier, or diluted by a carrier, of enclosed within a carrier that may be in the form of a capsule, sachet, paper or other container. When the carrier serves as a diluent, it may be a solid, semisolid, or liquid material that acts as a vehicle, excipient of medium for the active ingredient. Thus, the composition can be in the form of tablets, pills, powders, lozenges, sachets, cachets, elixirs, emulsions, solutions, syrups, suspensions, soft and hard gelatin capsules, sterile injectable solutions, and sterile packaged powders.

Some examples of suitable carriers, excipients, and diluents include lactose, dextrose, sucrose, sorbitol, mannitol, starches, gum acacia, calcium phosphate alginates, calcium salicate, microcrystalline cellulose, polyvinylpyrrolidone, cellulose, tragacanth, gelatin, syrup, methyl cellulose, methyl- and propylhydroxybenzoates, talc, magnesium stearate, water, and mineral oil. The compositions can additionally include lubricating agents, wetting agents, emulsifying and suspending agents, preserving agents, sweetening agents or flavoring agents. The compositions may be formulated so as to provide quick, sustained, or delayed release of the active ingredient after administration to the patient by employing procedures well known in the art.

For oral administration, a compound can be admixed with carriers and diluents, molded into tablets, or enclosed in gelatin capsules. The mixtures can alternatively be dissolved in liquids such as 10% aqueous glucose solution, isotonic saline, sterile water, or the like, and administered intravenously or by injection.

The local delivery of inhibitory amounts of an active compound for the treatment of cancer can be a variety of techniques that administer the compound at or near the proliferative site. Examples of local delivery techniques are not intended to be limiting but to be illustrative of the techniques available. Examples include local delivery catheters, site specific carriers, implants, direct injection, or direct applications. Local delivery by a catheter allows the administration of a pharmaceutical agent directly to the proliferative site.

Local delivery by an implant describes the surgical placement of a matrix that contains the pharmaceutical agent into the proliferative lesion. The implanted matrix releases the pharmaceutical agent by diffusion, chemical reaction, or solvent activators.

Another example is the delivery of a pharmaceutical agent by polymeric endoluminal sealing. This technique uses a catheter to apply a polymeric implant to the interior surface of the lumen. The pharmaceutical agent incorporated into the biodegradable polymer implant is thereby released at the surgical site. It is described in PCT WO 90/01969 (Schindler, Aug. 23, 1989).

A final example of local delivery by an implant is by direct injection of vesicles or microparticulates into the proliferative site. These microparticles may be composed of substances such as proteins, lipids, carbohydrates or synthetic polymers. These microparticulates have the pharmaceutical agent incorporated throughout the microparticle or over the microparticle as a coating. Delivery systems incorporating microparticles are described in Lange, Science, 249:1527-1533 (1990) and Mathiowitz et al., J. App. Poly. Sci., 26:809 (1981).

Local delivery by site specific carriers describes attaching the pharmaceutical agent to a carrier which will direct the drug to the proliferative lesion. Examples of this delivery technique include the use of carriers such as a protein ligand or a monoclonal antibody.

Local delivery by direct application includes the use of topical applications. An example of a local delivery by direct application is applying the pharmaceutical agent to the arterial tumor or area left behind after resection of the tumor.

The proliferation of cells may be dependent on the PI-3 kinase-Akt-mTOR signaling pathway. In addition, signaling through PI-3 kinase and Akt appears to inhibit apoptosis. The ability of wortmannin analogs and metabolites thereof to inhibit PI-3 kinase and mTOR may be expressed as the dose that causes 50% inhibition ($IC_{50}$). Growth inhibition of human MCF-7 breast cancer cells was measured over 4 days using the MTT assay, and results are expressed as the dose to cause 50% inhibition ($IC_{50}$). The MTT assay is a standard colorimetric assay for measuring cellular proliferation (cell growth). It is universally used to determine cytotoxicity of potential medicinal agents and other toxic materials. Yellow MTT (3-(4,5-Dimethylthiazol-2-yl)-2,5-diphenyltetrazolium bromide) is reduced to purple formazan in the mitochondria of living cells. This reduction takes place only when mitochondrial reductase enzymes are active, and therefore conversion is directly related to the number of viable (living) cells. Groups of 3 C57BL6 mice were administered wortmannin at doses of 1, 2 or 3 mg/kg or the analogues at 1, 3, 9 or 18 mg/kg by the intraperitoneal route daily for 4 days. The animals were killed 24 Hours after the last dose and differential blood counts and serum chemistry were determined. The major toxicities observed were liver toxicity and lymphocytopenia with decreased red blood counts and increased serum glucose at higher doses. Toxicities are measured at the maximum tolerated dose or the highest dose tested. Liver toxicity is measured as the mean percent increase in serum ALT and AST expressed relative to wortmannin as 1.0. Alanine aminotransferease (ALT) and aspartate aminotransferease (AST) are enzymes located in liver cells that leak out into the general circulation when liver cells are injured. Lymphocytopenia is expressed as the percent decrease in lymphocyte counts relative to wortmannin as 1.0. A low liver toxicity and a high lymphocyte toxicity as a surrogate for inhibition of tumor cell growth is the desirable feature.

Figure 7A:
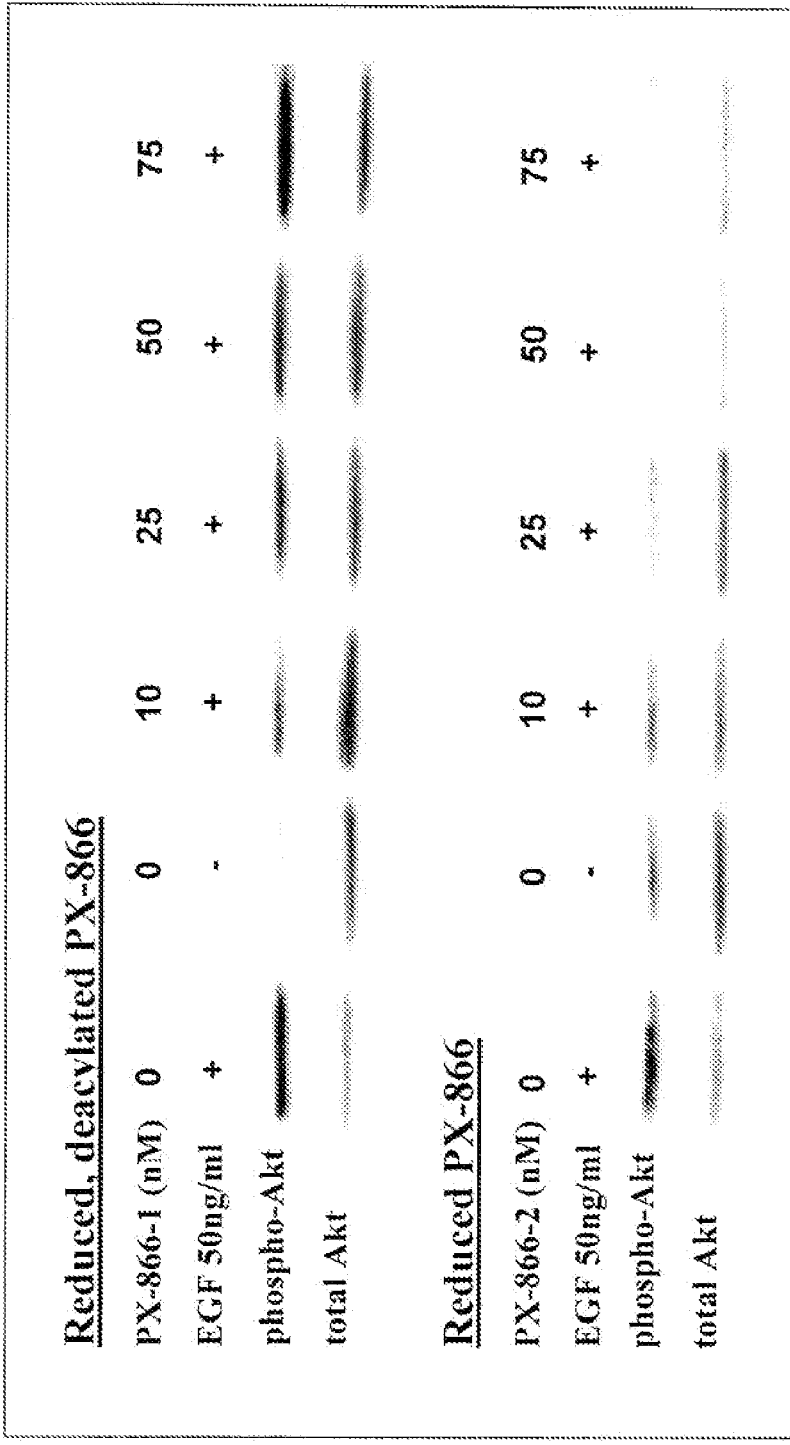
FIG. 7A illustrates the ability of two metabolites of an analog of wortmannin (PX-866) of the present disclosure to inhibit the epidermal growth factor-dependent activation of Akt as measured in HT-29 colon cancer cells. Shown is a western hybridization using anti-phospho-Ser$^{473}$-Akt antibodies.
Figure 7B:
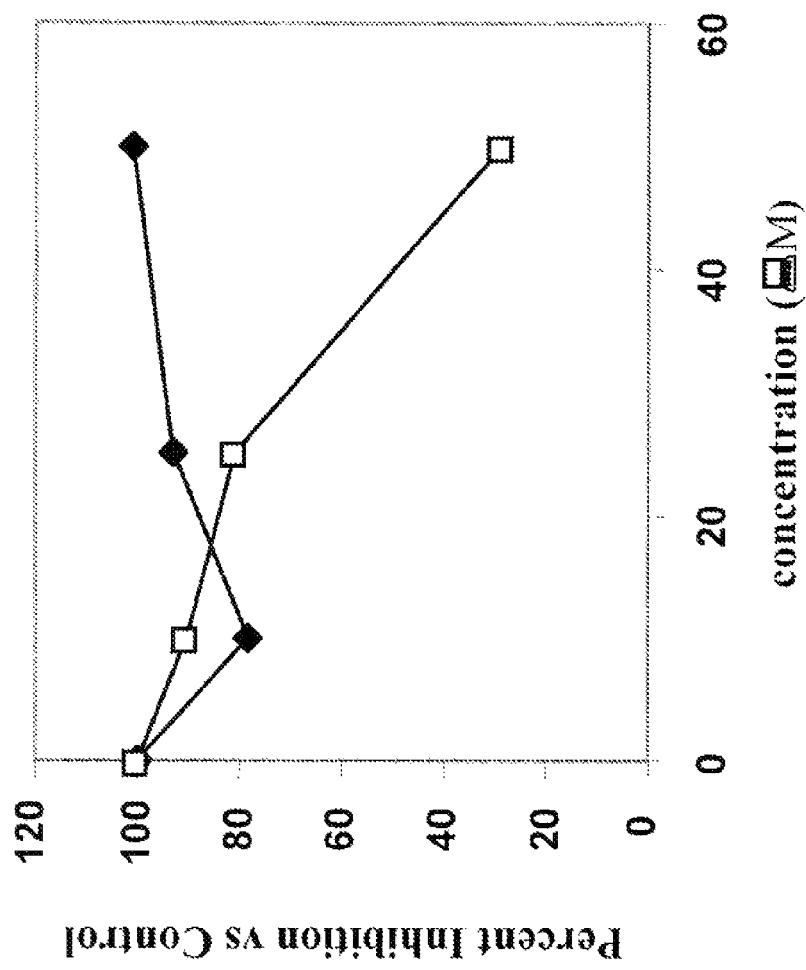
FIG. 7B illustrates the ability of two metabolites of an analog of wortmannin (PX-866) of the present disclosure to inhibit the epidermal growth factor dependent activation of Akt as measured in HT-29 colon cancer cells. Shown is quantified data from a densitometry scan of the western hybridization of FIG. 7A expressed as a ratio of phospho-Ser$^{473}$-Akt to total Akt as a percentage versus the control with no drug: (□) 17-hydroxy PX-866 (PX-866-2) and (♦) 11-deacetylated, 17-hydroxy PX-866 (PX-866-1).

Based on results from these studies (Table 1), wortmannin and wortmannin analogs are inhibitors of PI-3 kinase and are observed to inhibit cell growth and cell survival. Moreover, these wortmannin PI-3 kinase inhibitors also inhibit the local inflammatory response, especially in the case of a bioprosthetic implant, which may be a favorable factor for long-term engraftment or other bioprosthetic implant. In principle, the wortmannin analogs may be ideal agents for inducing a temporary block of the PI-3 kinase-Akt-mTOR pathway.

ties against PI-3 kinase that may be similar to or better than those of wortmannin (see Example 7). The ability of the metabolites of wortmannin analogs to inhibit the epidermal growth factor dependent activation of Akt was measured in HT-29 colon cancer cells by western blot hybridization using an anti-phospho-Ser$^{473}$-Akt antibody (FIG. 7A). Quantitation of the blots to give the ratio of phospho-Ser$^{473}$-Akt to total Akt is shown in FIG. 7B. The calculated inhibitory concentration 50% ($IC_{50}$) for 17-hydroxy PX-866 (□) was 40 nM and for 11-deacetylated,17-hydroxy PX-866 (♦) was greater than 70 nM. Under the same assay conditions, the $IC_{50}$ for parent PX-866 was 27 nM (not shown). Thus 17-hydroxy PX-866 (PX-866-2) has the same cell phosphor-Ser$^{473}$-Akt inhibitory activity as PX-866, while 11-deacetylated,17-hydroxy PX-866 (PX-866-1) is much less active.

Figure 8:
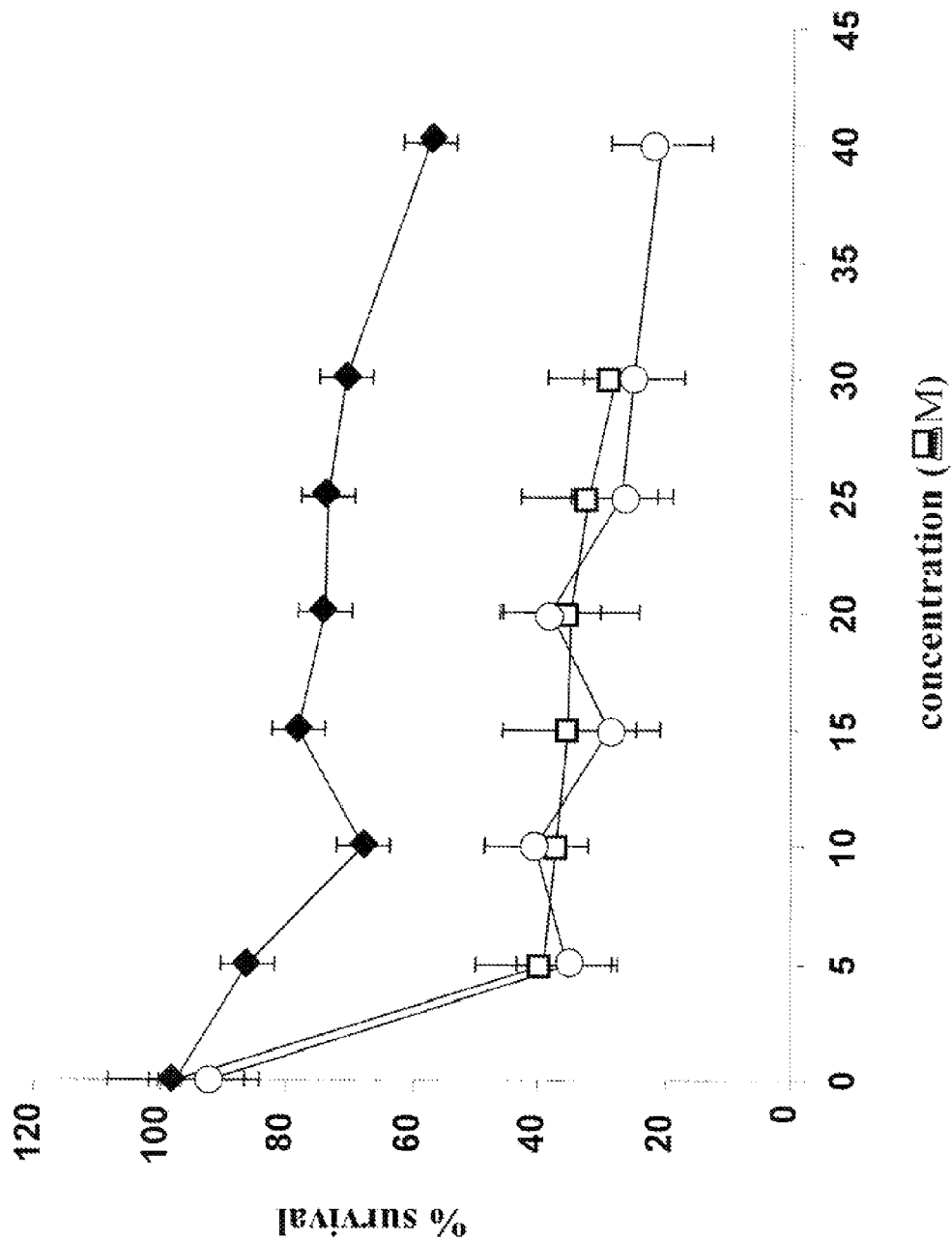
FIG. 8 illustrates the cytotoxicity of PX-866 metabolites (PX-866-1 and PX-866-2) of the present disclosure to HT-29 colon cancer cells: (○) PX-866; (□) PX-866-2; (♦) PX-866-1.

The cytotoxicity of the metabolites of wortmannin analogs is shown in FIG. 8. HT-29Human colon cancer cells were grown in Dulbecco's modification of Eagles medium (DMEM) with 10% fetal calf serum to 25% confluency, then grown a further 3 days in fresh medium containing (○) PX-866, (□) PX-866-2 or (♦) PX-866-1. The compounds were added from a 10 mg/ml stock solution in ethanol. Cell number was determined after 3 days by flow cytometry using a Guava EasyCyte Plus flow cytometer (Guava Technologies). The results are expressed as cell number at the end of the assay aspercent of the control value with no drug. Values are the mean of 3 determinations and bars are standard deviation. The growth inhibitory concentration 50% ($IC_{50}$) for PX-866 was 4.0 μM, for PX-866-1 was 4.5 μM, and for PX-866-2 was greater than 50 μM. Thus PX-8660-2Has the same cell growth inhibitory activity as PX-866 but PX-866-1 is much less active.

Figure 9:
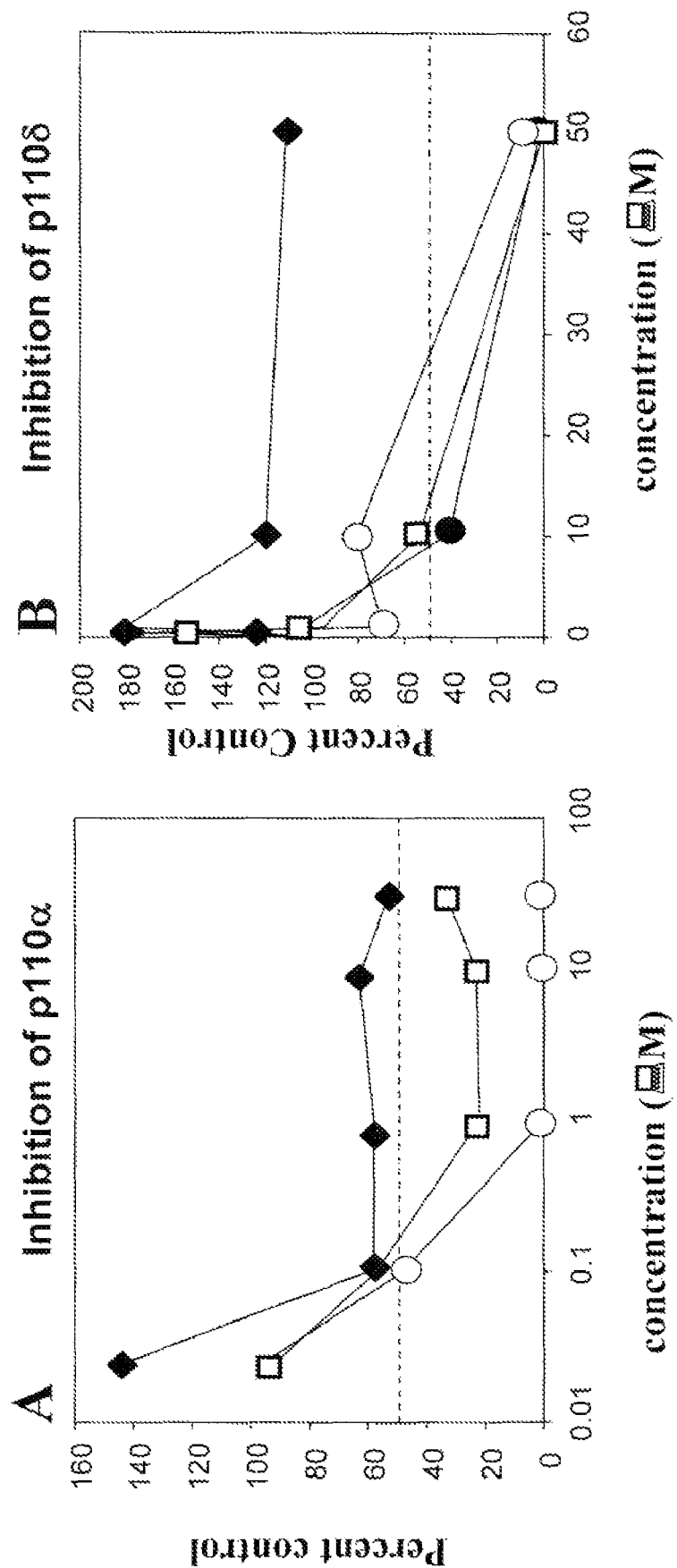
FIG. 9A illustrates inhibition of recombinant PI-3 kinase (recombinant bovine p110α/p85α) signaling by PX-866 and its metabolites: (○) PX-866, (●) wortmannin, (□) PX-866-2 or (♦) PX-866-1.
FIG. 9B illustrates inhibition of recombinant PI-3 kinase (recombinant human p110δ/p85α) signaling by PX-866 and its metabolites: (○) PX-866, (●) wortmannin, (□) PX-866-2 or (♦) PX-866-1.

Inhibition of recombinant PI-3 kinase by PX-866 and its metabolites is shown in FIG. 9. PI-3 kinase activity was measured by the [$^{32}$P]γ-ATP dependent phosphorylation of

TABLE 1

Activity and in-vivo toxicity of wortmannin and wortmannin analogs

| Compound | Maximum tolerated dose (mg/ml) | PI-3 kinase inhibition $IC_{50}$ (nM) | mTOR inhibition $IC_{50}$ (μM) | Cytotoxicity: NCl cell panel $IC_{50}$ (μM) | Lymphocyte toxicity relative to wortmannin | Liver toxicity relative to wortmannin |
|---|---|---|---|---|---|---|
| Wortmannin | 2.5 | 0.3 | 0.1 | 8.9 | 1.0 | 1.0 |
| PX-866 | 20 | 0.5 | >3 | 2.2 | 2.2 | 0.3 |
| PX-867 | 20 | 1.1 | >3 | 0.5 | 2.4 | 0.3 |

It has further been observed in pharmacokinetic studies as set forth in U.S. patent application Ser. No. 11/178,553, entitled "Wortmannin Analogs and Methods and Methods of Using the Same Combination with Chemotherapeutic Agents" filed Jul. 11, 2005, herein incorporated by reference in its entirety, that the blood levels of PX-866 and PX-867 following oral administration are low. Both PX-866 and PX-867 may be more effective at lower oral doses than when administered intravenously. While not wishing to be bound by theory, it is hypothesized that this effect is attributable to active, and potentially more potent, metabolites of PX-866 and PX-867. Embodiments of the present disclosure provide novel metabolites of wortmannin and metabolites of the wortmannin analogs, and their use as inhibitors of PI-3 kinase. Further embodiments of the disclosure provide for use of these novel metabolites as anti-cancer and anti-tumor agents.

These metabolites, examples of which are shown in FIGS. 1-3, have been shown herein to demonstrate inhibitory activiphosphatidylinositol as previously described (Ihle et al. (2005) Mol. Cancer Ther. 4(9):1349-1357). FIG. 9A shows results of the assay using recombinant bovine p110α/p85α (Jena Bioscience,Jena, Germany) and FIG. 9B shows results of the assay using recombinant human p110δ/p85α (Upstate, Charlottesville, Va.). Inhibition was measured using (○) PX-866, (●) wortmannin, (□) PX-866-2 or (♦) PX-866-1. The results show that PX-866-2 is as active as PX-866 or wortmannin at inhibiting the p110α and p110δ isoforms of PI-3 kinase but the PX-866-1 was considerably less active.

Thus, an embodiment of the disclosure provides a method of inhibiting PI-3 kinase activity in mammals comprising administering to a mammal an effective amount of a compound of formula 2 or 3, as shown in FIG. 1. A preferred embodiment of the disclosure provides a method of inhibiting PI-3 kinase activity in mammals comprising administering to a mammal an effective amount of a compound of structure 5 or 7,a shown in FIG. 2. A more preferred embodiment of the disclosure provides a method of inhibiting PI-3 kinase activity in mammals comprising administering to a mammal an effective amount of a compound of structure 9 or 10, as shown in FIG. 3.

Another embodiment of the disclosure provides a method of inhibiting PI-3 kinase activity in a cell comprising contacting the cell with a compound of formula 2 or 3, as shown in FIG. 1, whereby the compound inhibits PI-3 kinase. A preferred embodiment of the disclosure provides a method of inhibiting PI-3 kinase activity in a cell comprising contacting the cell with a compound of structure 5 or 7, as shown in FIG. 2, whereby the compound inhibits PI-3 kinase. A more preferred embodiment of the disclosure provides a method of inhibiting PI-3 kinase activity in a cell comprising contacting the cell with a compound of structure 9 or 10, as shown in FIG. 3, whereby the compound inhibits PI-3 kinase.

Since PI-3 kinase activity may be a factor in certain types of cancers, the present disclosure also provides for use of the compounds as anti-tumor agents, anti-cancer agents, and for pharmaceutical compositions useful for the treatment of such tumors or cancers. Cancers treatable by compounds of this disclosure may include, but are not limited to, breast cancer, lung cancer, head and neck cancer, brain cancer, abdominal cancer, colon cancer, colorectal cancer, esophageal cancer, gastrointestinal cancer, glioma, liver cancer, tongue cancer, neuroblastoma, osteosarcoma, ovarian cancer, pancreatic cancer, renal cancer, prostate cancer, retinoblastoma, Wilm's tumor, multiple myeloma, skin cancer, lymphoma and blood cancer. As such, an embodiment of the disclosure provides for a method of treating cancer comprising administering to a subject a therapeutically effective amount of a compound of formula 2 or 3, as shown in FIG. 1. The cancer treated by the compound of formula 2 or 3 may be breast cancer, lung cancer, head and neck cancer, brain cancer, abdominal cancer, colon cancer, colorectal cancer, esophageal cancer, gastrointestinal cancer, glioma, liver cancer, tongue cancer, neuroblastoma, osteosarcoma, ovarian cancer, pancreatic cancer, renal cancer, prostate cancer, retinoblastoma, Wilm's tumor, multiple myeloma, skin cancer, lymphoma, and blood cancer. Preferably, the cancer treated by the compound of formula 2 or 3 is colon cancer. A preferred embodiment of the disclosure provides for a method of treating cancer comprising administering to a subject a therapeutically effective amount of a compound of structure 5 or 7, as shown in FIG. 2. In a preferred embodiment, the cancer treated by the compound of structure 5 or 7, is colon cancer. A more preferred embodiment of the disclosure provides for a method of treating cancer comprising administering to a subject a therapeutically effective amount of a compound of structure 9 or 10, as shown in FIG. 3. In this more preferred embodiment, the cancer treated by the compound of structure 9 or 10 is colon cancer.

Embodiments of the disclosure also provide for using a pharmaceutical composition to treat tumor cell proliferation or tumor cell growth by administering to a mammal a pharmaceutical composition containing a compound of formula 2 or 3, as shown in FIG. 1. A preferred embodiment of the disclosure provides a method of treating tumor cell proliferation or tumor cell growth comprising administering to a mammal a pharmaceutical composition containing a compound of structure 5 or 7, as shown in FIG. 2. A more preferred embodiment of the disclosure provides a method of treating tumor cell proliferation or tumor cell growth comprising administering to a mammal a pharmaceutical composition containing a compound of structure 9 or 10, as shown in FIG. 3.

Embodiments of the disclosure also provide a method of treating tumor cell proliferation or tumor cell growth comprising administering to a subject an effective amount of a compound of formula 2 or 3, as shown in FIG. 1. A preferred embodiment of the disclosure provides a method of treating tumor cell proliferation or tumor cell growth comprising administering to a subject an effective amount of a compound of structure 5 or 7, as shown in FIG. 2. A more preferred embodiment of the disclosure provides a method of treating tumor cell proliferation or tumor cell growth comprising administering to a subject an effective amount of a compound of structure 9 or 10, as shown in FIG. 3.

In some aspects of the invention, the compounds of the present disclosure are derivatives referred to as prodrugs. The expression "prodrug" denotes a derivative of a known direct acting drug, which derivative has enhanced delivery characteristics and therapeutic value as compared to the drug, and is transformed into the active drug by an enzymatic or chemical process.

When any variable occurs more than one time in any constituent or in any of the compounds recited for any of the formula above, its definition on each occurrence is independent of its definition at every other occurrence. Also, combinations of substituents and/or variables are permissible only if such combinations result in stable compounds.

It is understood that the present invention encompasses the use of stereoisomers, diastereomers and optical isomers of the compounds of the present invention, as well as mixtures thereof. Additionally, it is understood that stereoisomers, diastereomers and optical isomers of the compounds of the present invention, and mixtures thereof, are within the scope of the invention. By way of non-limiting example, the mixture may be a racemate or the mixture may comprise unequal proportions of one particular stereoisomer over the other. Additionally, the compounds of the present invention may be provided as a substantially pure stereoisomers, diastereomers and optical isomers.

In another aspect of the invention, the compounds can be provided in the form of an acceptable salt (i.e., a pharmaceutically acceptable salt). Salts can be provided for pharmaceutical use, or as an intermediate in preparing the pharmaceutically desired form of the compound. For example, one salt that can be considered to be acceptable is the hydrochloride acid addition salt. For example, chloride ion can be present as a counter ion for compounds having cationic side chains. Hydrochloride acid addition salts are often acceptable salts when the pharmaceutically active agent has an amine group that can be protonated.

For example, in some aspects, the invention is directed to a pharmaceutical composition comprising a compound, as defined above, and a pharmaceutically acceptable carrier or diluent, or an effective amount of a pharmaceutical composition comprising a compound as defined above.

The compounds of the present invention can be administered in the conventional manner by any route where they are active. Administration can be systemic, topical, or oral. For example, administration can be, but is not limited to, parenteral, subcutaneous, intravenous, intramuscular, intraperitoneal, transdermal, oral, buccal, or ocular routes, or intravaginally, by inhalation, by depot injections, or by implants. Thus, modes of administration for the compounds of the present invention (either alone or in combination with other pharmaceuticals) can be, but are not limited, to, sublingual, injectable (including short-acting, depot, implant and pellet forms injected subcutaneously or intramuscularly), or by use of vaginal creams, suppositories, pessaries, vaginal rings, rectal suppositories, intrauterine devices, and transdermal forms such as patches and creams.

Specific modes of administration will depend of the indication. The selection of the specific route of administration and the dose regimen is to be adjusted or titrated by the clinician according to methods known to the clinician in order to obtain the optimal clinical response. The amount of compound to be administered is that amount which is therapeutically effective. The dosage to be administered will depend on the characteristics of the subject being treated, e.g., the particular animal treated, age, weight, health, types of concurrent treatment, if any, and frequency of treatments, and can be easily determined by one of skill in the art (e.g., by the clinician).

Pharmaceutical compositions containing the compounds of the present invention and a suitable carrier can be solid dosage forms which include, but are not limited to, tablets, capsules, cachets, pellets, pills, powders, fluid emulsions, fluid suspensions, semi-solids, ointments, pastes, creams, gels and jellies, and foams; and parenteral dosage forms which include, but are not limited to, solutions, suspensions, emulsions, and dry powder, comprising an effective amount of a polymer or copolymer of the present invention. It is also known in the art that the active ingredients can be contained in such compositions with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The means and methods for administration are known in the art and an artisan can refer to various pharmacologic references for guidance. For example, *Modern Pharmaceutics*, Banker & Rhodes, Marcel Dekker, Inc. (1979); and *Goodman & Gilman's The Pharmaceutical Basis of Therapeutics*, 6th Edition, MacMillan Publishing Co., New York (1980) can be consulted.

The compounds of the present invention can be formulated for parenteral administration by injection, e.g., by bolus injection or continuous infusion. The compounds can be administered by continuous infusion subcutaneously over a period of about 15 minutes to about 24 Hours. Compositions for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents.

For oral administration, the compounds can be formulated readily by combining these compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by adding a solid excipient, optionally grinding the resulting mixture, and processing the mixture of granules, after adding suitable auxiliaries, if desired, to obtain tablets or dragee cores. Suitable excipients include, but are not limited to, fillers such as sugars, including, but are not limited to, lactose, sucrose, mannitol, and sorbitol; cellulose preparations such as, but not limited to, lactose, sucrose, mannitol, and sorbitol; cellulose preparations such as, but not limited to, maize starch, wheat starch, rice starch, potato starch, gelatin, gum tragacanth, methyl cellulose, hydroxypropylmethyl-cellulose, sodium carboxymethylcellulose, and polyvinylpyrrolidone (PVP). If desired, disintegrating agents can be added, such as, but not limited to, the cross-linked polyvinyl pyrrolidone, agar, or alginic acid or a salt thereof such as sodium alginate.

Dragee cores can be provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations which can be used orally include, but are not limited to, push-fit capsules made of gelatin, as well as soft, sealed capsules made of gelatin and a plasticizer, such as glycerol or sorbitol. The push-fit capsules can contain the active ingredients in admixture with filler such as, e.g., lactose, binders such as, e.g., starches, and/or lubricants such as, e.g., talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All compositions for oral administration should be in dosages suitable for such administration.

For buccal administration, the compositions can take the form of, e.g., tablets or lozenges formulated in a conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The compounds of the present invention can also be formulated in rectal compositions such as suppositories or retention enemas, e.g., containing conventional suppository bases such as cocoa butter or other glycerides.

In addition to the compositions described previously, the compounds of the present invention can also be formulated as a depot preparation. Such long acting compositions can be administered by implantation (for example subcutaneously or intramuscularly) or by intramuscular injection.

Depot injections can be administered at about 1 to about 6 months or longer intervals. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

In transdermal administration, the compounds of the present invention, for example, can be applied to a plaster, or can be applied by transdermal, therapeutic systems that are consequently supplied to the organism.

Pharmaceutical compositions of the compounds also can comprise suitable solid or gel phase carriers or excipients. Examples of such carriers or excipients include but are not limited to calcium carbonate, calcium phosphate, various sugars, starches, cellulose derivatives, gelatin, and polymers such as, e.g., polyethylene glycols.

The compounds of the present invention can also be administered in combination with other active ingredients, such as, for example, adjuvants, protease inhibitors, or other compatible drugs or compounds where such combination is seen to be desirable or advantageous in achieving the desired effects of the methods described herein.

This invention and embodiments illustrating the method and materials used may be further understood by reference to the following non-limiting examples.

EXAMPLE 1

This example illustrates an embodiment of a method of producing PX-866: Acetic acid 4-diallylaminomethylene-6-hydroxy-1-α-methoxymethyl-10β,13β-dimethyl-3,7,17-trioxo-1,3,4,7,10,11β,12,13,14α,15,16,17-dodecahydro-2-oxa-cyclopenta[α] phenanthren-11-yl ester.

To a solution of wortmannin (10.7 mg, 25.0 μmol) in $CH_2Cl_2$ (125 μL) was added a freshly prepared 0.2 M stock solution of diallylamine (138 μL, 27.5 μmol) in $CH_2Cl_2$. The reaction mixture was stirred at room temperature for 1 h. The solvent and excess amine were removed in vacuo, and the product was purified via chromatography on $SiO_2$ (hexanes/ethyl acetate, 1:9) to give PX-866 (9.0 mg, 17 μmol, 68%) as an orange oil. The product was analyzed by several experimental methods and shown to be of the correct structure and of high purity as: $[\alpha]_D$ −630 (c 0.0015, $CH_2Cl_2$, 23° C.); IR (KBr) 3391, 1743, 1695, 1685, 1622, 1569, 1222, 1111, 1100 $cm^{-1}$; $^1H$ NMR δ 8.20 (s, 1H), 6.81 (s, 1H), 6.06 (dd, 1H, J=7.4, 4.8 Hz), 5.85 (br s, 1H), 5.62 (br, 1H), 5.44-5.04 (m, 4H), 4.48 (dd, 1H, J=7.2, 1.9 Hz), 4.05-3.60 (m, 4H), 3.26 (s, 3H), 3.27-3.20 (m, 1H), 3.16 (dd, 1H, J=10.9, 7.2 Hz), 3.00-2.90 (m, 2H), 2.59 (dd, 1H, J=19.4, 8.6 Hz), 2.40 (dd, 1H, J=14.4, 7.7 Hz), 2.35-2.07 (m, 2H), 2.07 (s, 3H), 1.83 (dd, 1H, J=14.4, 4.7 Hz), 1.54 (s, 3H), 0.86 (s, 3H); $^{13}C$ NMR δ 217.0, 178.5, 169.6, 164.8, 156.3, 151.5, 139.0, 136.9, 132.2, 131.3, 127.7 (2 C), 119.2, 89.0, 81.9, 73.1, 67.6, 59.1, 50.9 (2 C), 48.9, 42.3, 42.2, 37.5, 36.0, 24.6, 22.2, 20.8, 16.1; MS (EI) m/z (rel. intensity) 525 (M', 11), 466 (17), 391 (15), 350 (14), 323 (13), 266 (17), 239 (17), 60 (100); HRMS (EI) calculated for $C_{29}H_{35}NO_8$ 525.2363; found 525.2386.

EXAMPLE 2

This example illustrates an embodiment of a method of producing PX-867: Acetic acid 6-hydroxy-1α-methoxymethyl-10β, 13β-dimethyl-3,7,17-trioxo-4-pyrrolidin-1-yl-methylene-1,3,4,7,10,11β,12,13,14α,15,16,17-dodecahydro-2-oxa-cyclopenta[α] phenanthren-11-yl.

To a solution of wortmannin (30.0 mg, 70.0 μmol) in $CH_2Cl_2$ (200 μL) was added pyrrolidine (7.0 μL, 84 μmol) in $CH_2Cl_2$. The reaction mixture was stirred at room temperature for 1 h. The solvent and excess thiol were removed in vacuo and the product was purified by chromatography on $SiO_2$ (hexanes/ethyl acetate 9:1, then 1:1) to give PX-867 (30.0 mg, 60.6 μmol, 86%) as an orange oil. The product was analyzed by several experimental methods and shown to be of the correct structure and of high purify as: $[\alpha]_D$ −390 (c 0.0073, $CH_2Cl_2$, 23° C.); IR (KBr) 3337, 1740, 1684, 1617, 1570, 1261, 1221, 1099, 1018 $cm^{-1}$; $^1H$ NMR δ 8.29 (s, 1H), 6.72 (s, 1H), 6.07 (dd, 1H, J=6.9,4.8 Hz), 4.47 (dd, 1H, J=7.0, 1.9 Hz), 3.80-3.70 (m, 2H), 3.25 (s, 3H), 3.25-3.14 (m, 2H), 3.02-2.90 (m, 2H), 2.69 (br s, 1H), 2.58 (dd, 1H), J=19.1, 8.4 Hz), 2.39 (dd, 1H, J=14.6. 7.8 Hz), 2.32-2.08 (m, 2H), 2.06 (s, 3H), 1.99-1.95 (m, 5H), 1.84 (dd, 1H, J=14.5, 4.2 Hz), 1.56 (s, 3H), 0.86 (s, 3H); $^{13}C$ NMR δ 217.5, 178.9, 169.9, 164.9, 153.9, 151.3, 137.6, 137.1, 129.2, 89.4, 82.1, 73.3, 67.7, 59.3, 55.2, 49.2 (2 C), 42.6, 42.4, 37.8, 36.3, 25.6 (2 C), 24.5, 22.4, 21.0, 16.3; MS (EI) m/z (rel. intensity) 499 (M$^+$, 1), 439 (2), 365 (7), 167 (35), 149 (100); HRMS (EI) calculated for $C_{27}H_{33}NO_8$ 499.2206; found 499.2191.

EXAMPLE 3

This example illustrates one embodiment of a method of producing PX-867 and metabolites thereof. Wortmannin (4) was obtained from Synexa Life Sciences Company for the synthesis of PX-867. HPLC analysis of this wortmannin shows a more polar impurity. Thin layer chromatography (TLC) of the sample was run using ethyl acetate as the eluent to visualize the more polar impurity. The polar impurity was characterized using high resolution NMR spectroscopy and shown to be 17β-hydroxy wortmannin (5 below).

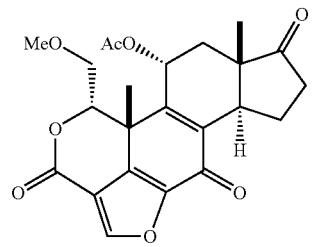

4

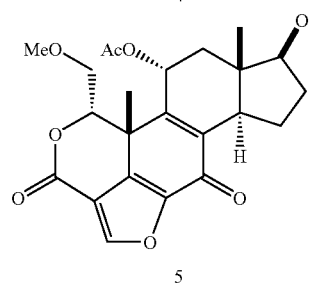

5

The pure wortmannin (4) obtained after the TLC was converted to PX-867 (6) according to Scheme 1: a solution of pyrrolidine in dichloromethane is added to a solution of wortmannin in dichloromethane. PX-867 (6) was obtained in pure form and very high (~95%) yield. While the PX-867 obtained from certain batches of wortmannin did not require further purification, some batches shows that traces of pyrrolidine still remained, even after keeping the compound under vacuum overnight. The purification of PX-867 (6) was achieved by gravity column chromatography on silica gel using ethyl acetate as an eluent.

scheme 1

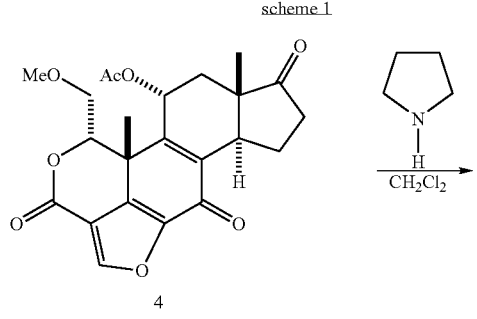

4

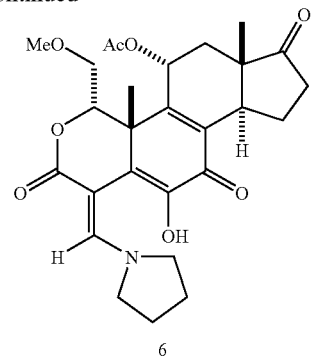

6

General Synthesis of PX-867: To a solution of wortmannin (4) (970 mg, 2.26 μmol) in $CH_2Cl_2$ (12 μL) at 0° C. was added a solution of anhydrous pyrrolidine (0.2 M, 12 μL, 2.49 μmol) in $CH_2Cl_2$. The reaction mixture was allowed to warm to room temperature and was stirred for 1H. The solvent and excess amine were removed under reduced pressure and the residue was chromatographed on silica gel. Elution with EtOAc gave 1.12 g (2.24 mmol, 99%), of PX-867 as an orange solid in quantitative yield. The $^1$H-NMR spectrum of the compound was consistent with the spectral data previously reported, an example of which is listed in Example 2.

The more polar impurity characterized as 17β-hydroxy wortmannin (5) (10 mg) was converted to 7 by a procedure similar to that described above for PX-867 and as depicted in Scheme 2. The $^1$H-NMR spectrum is in agreement with the structure of 7 (17β-hydroxy PX-867).

scheme 2

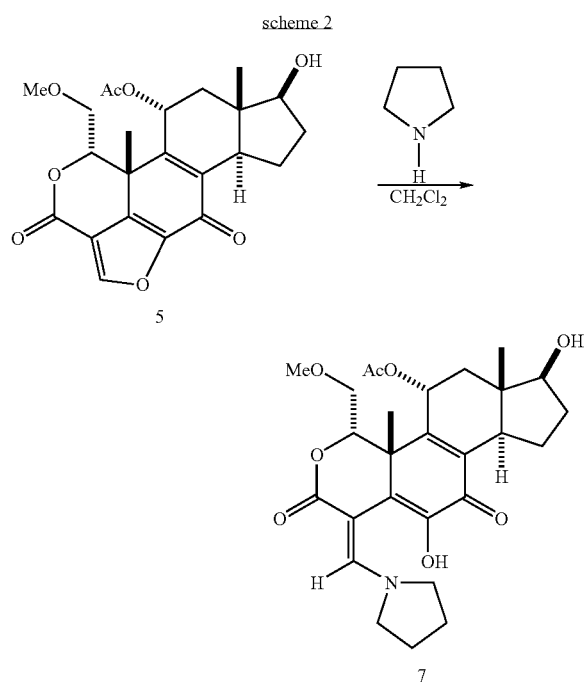

EXAMPLE 4

This example illustrates the development and validation of a sensitive HPLC analytical method for the quantitative determination of PX-866, at high concentrations, in buffer solutions to be used for stability studies. This method was used to assess the overall stability of PX-866 in a variety of buffer systems used for drug administration in preclinical studies. The intent was to determine the relative stability of PX-866 over a 24 Hour period for each of these solutions.

HPLC techniques with UV/Vis detection were used for the analysis of the stability samples of PX-866. PX-866 was dissolved in 100% methanol to a final concentration of 10 mg/mL. This solution was used as a stock to make the various test buffer solutions to be analyzed. The stock, in each case, was diluted 1:10 to a final storage concentration of 1 mg/mL with 5% dextrose for injection (D5W), sterile water for injection (SW), 0.9% sodium chloride for injection (NS), absolute ethanol (EtOH), and 20 mM sodium phosphate ($NaH_2PO_4$) buffer. Prior to analysis the test buffers were further diluted 1:100, to a final analytical concentration of 10 μg/mL, with 50:50 0.2% formic acid:methanol, v:v. 50 μL of each sample was then injected into the HPLC system (Alliance 2695 Separation Module, Waters, Milford, Mass.; see Table 2 for HPLC parameters) for analysis. The 2 Hour and 24 Hour test samples were stored, undiluted, at 4° C. prior to analysis while the 0 Hour samples wee immediately quantified following dilution.

Figure 4:
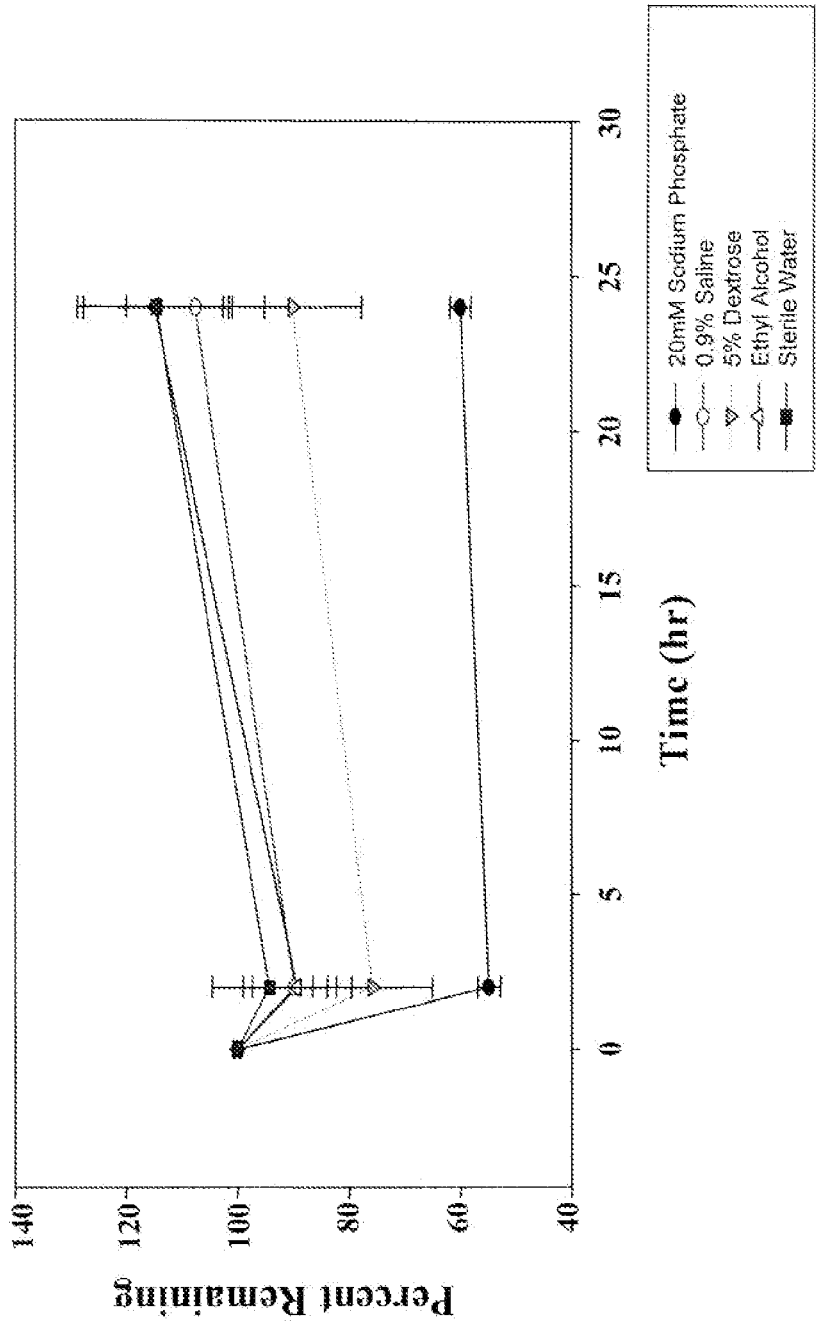
FIG. 4 illustrates the relative stability of the wortmannin analog PX-866 when stored at a concentration of 1 mg/ml for 24 Hours in various buffer systems.

Results found in FIG. 4 indicate differential buffer stability over the 24-hour observation period. These data demonstrate a rapid degradation of PX-866 in two of the buffer solutions. Within 2 Hours, both 20 mM sodium phosphate buffer (>60% remaining) and D5W (>80% remaining) demonstrate unsuitable drug loss. PX-866 was reasonably stable in NS, SW, and EtOH, showing <10% degradation after 2 Hours of storage. From 2 to 24 hours, the drug maintained relative stability, regardless of the buffer system employed.

TABLE 2

| HPLC parameters | |
|---|---|
| LC | Waters 2695 Separation Module (Alliance) |
| Detector | Waters 2487 Dual Absorbance at 254 nm |
| Analytical Column | Water Symmetry C8, 3.5 μm, 4.6 × 150 mm |
| Mobile Phase | 25:75 - 0.2% formic acid:methanol |
| Flow Rate | Isocratic; 0.6 ml/min @ 1950 psi |
| Retention Time | 22.4 minutes |

Figure 5:
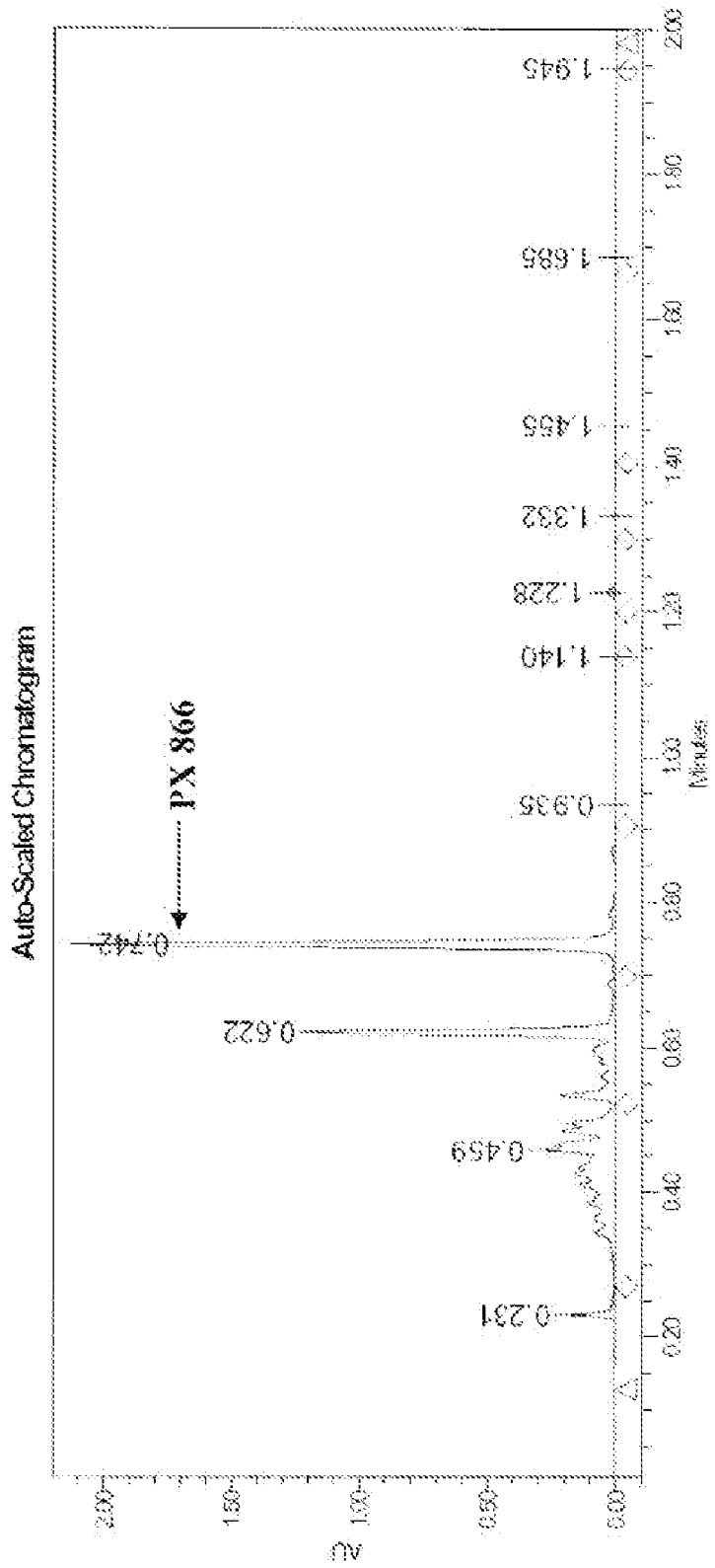
FIG. 5 illustrates an ultra-performance liquid chromatography (UPLC) separation profile for PX-866 in methanol. An injection of 2 ng of PX-866 (in 2 µl) elutes as a peak at 0.742 minutes that is well separated from baseline. The signal to noise ratio is in excess of 10,000. Detector response was saturated and in excess of 2.0 absorbance units, full scale. Peak width at half height is <2 seconds.

In addition, the capability of a new technique, UPLC, to rapidly quantify PX-866 in buffer solutions was examined. These systems can operate at backpressures of >15,000 psi, enabling very high flow rates (>10 ml/min) with increased resolution & sensitivity, the use of minimal sample volumes, and analytical run times of <1 minute. FIG. 5 shows an example chromatogram for PX-866 in organic solvents at a concentration of 1 μg/ml. An injection of 2 μl (2 ng on column) was made using an acetonitrile:water gradient and a $C_{18}$ column on a UPLC system with photodiode array detection (Waters Acquity, Milford, Mass.) yielding the chromatographic profile depicted in FIG. 5. The data suggest that UPLC methods may detect very small quantities of PX-866 and other wortmannin analogs and metabolites thereof, and may be useful in the study of the preclinical pharmacology of these compounds.

EXAMPLE 5

This example illustrates the determination of the metabolism of PX-866 in vitro in mouse, rat, dog and human liver microsomes and identification and structural analysis of the metabolites of PX-866 found therein.

Figure 6A:
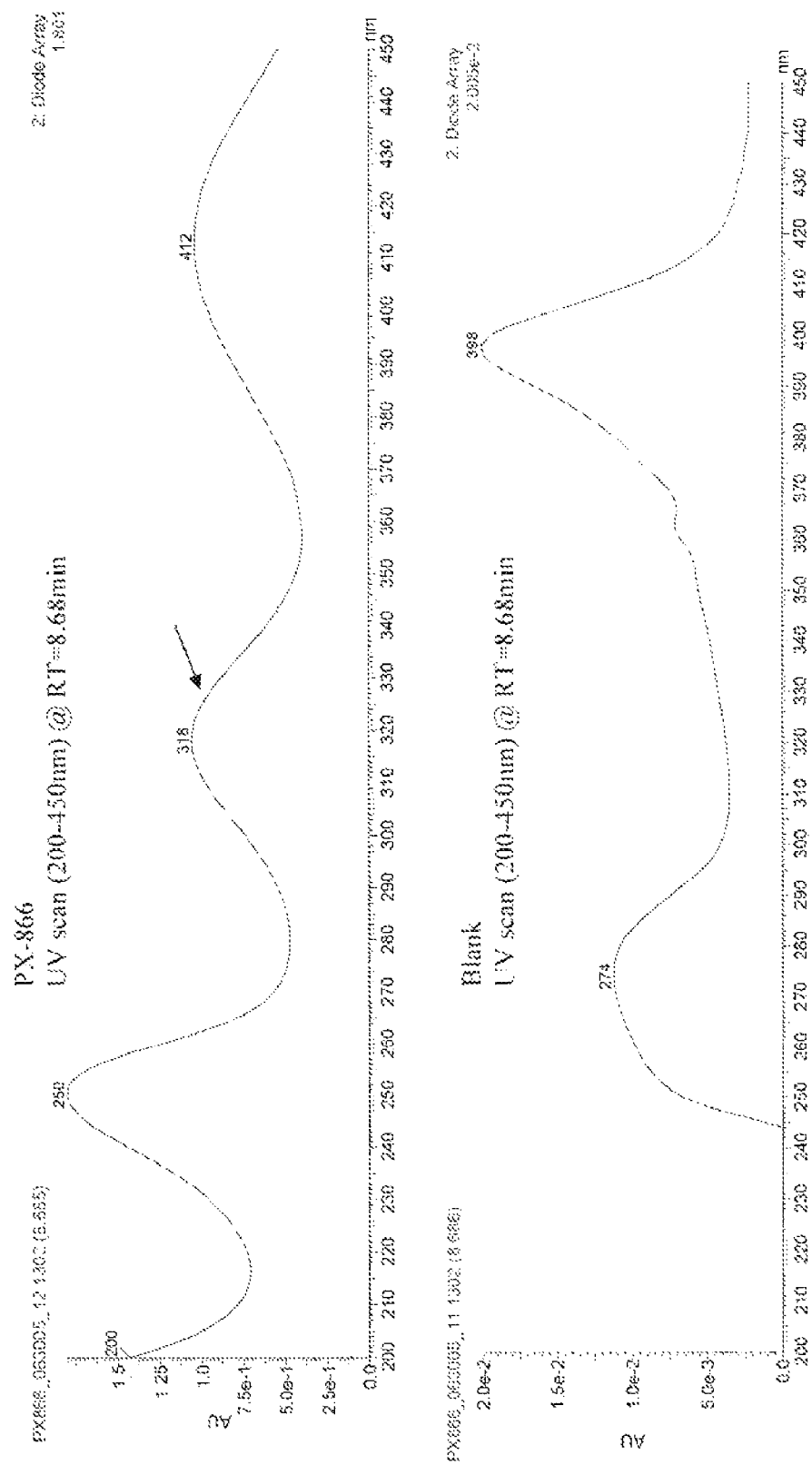
FIG. 6A illustrates the unique absorbance for PX-866 between 300-340 nm. The UV spectrographs show a range of UV absorbance for PX-866 with a λ maxima at 310 nm (top), as compared to blank matrix with no corresponding peak (bottom).
Figure 6B:
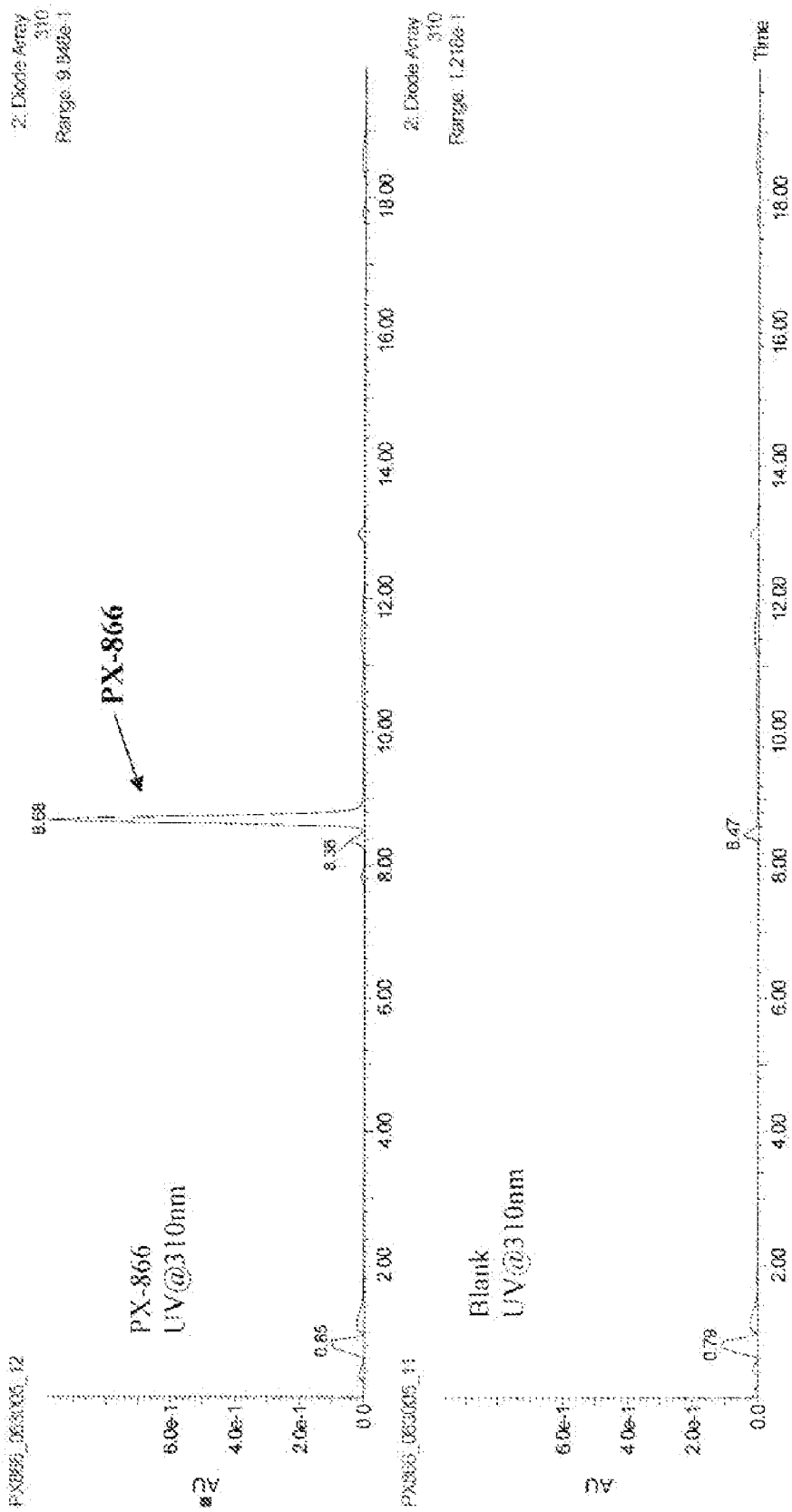
FIG. 6B illustrates a high-performance liquid chromatography (HPLC) separation profile for PX-866 as detected at the optimal wavelength of 310 nm. A 5.3 nMol injection showed a retention time for PX-866 of 8.68 min. No peaks above baseline are observed at that retention time for a blank rejection.
Figure 6C:
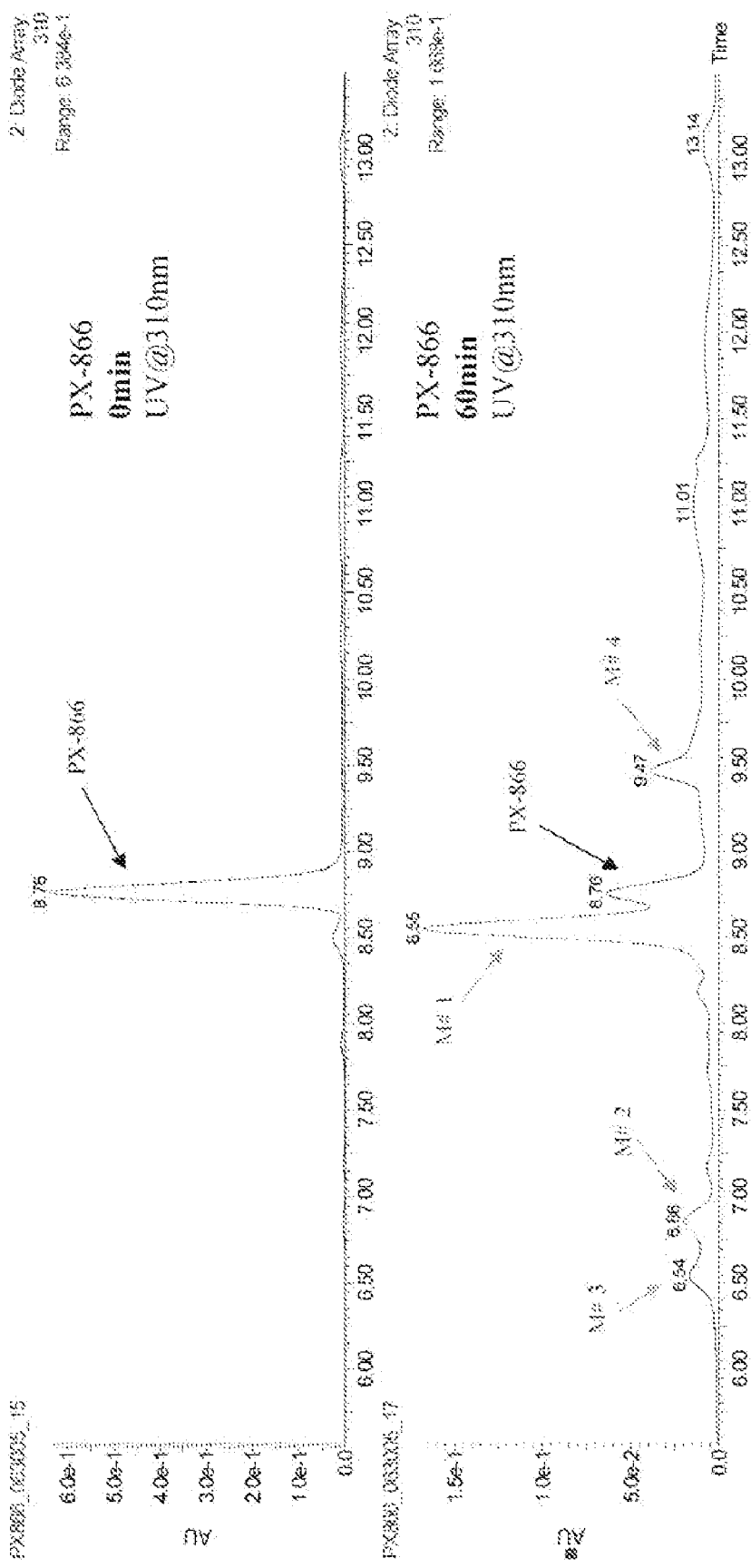
FIG. 6C illustrates identification of PX-866 metabolites by an HPLC separation profile (detected at 310 nm). Four metabolites can be identified (M#1-4), following completion of a 60 minute incubation. The UV absorbance peak area is largest for metabolite #1 (M#1; retention time on the column (RT)=8.55 min) as compared to the earlier eluting peaks. M#2 (RT=6.86 min), M#3 (RT=6.54 min), and the later eluting M#4 (RT=9.47 min).
Figure 6D:
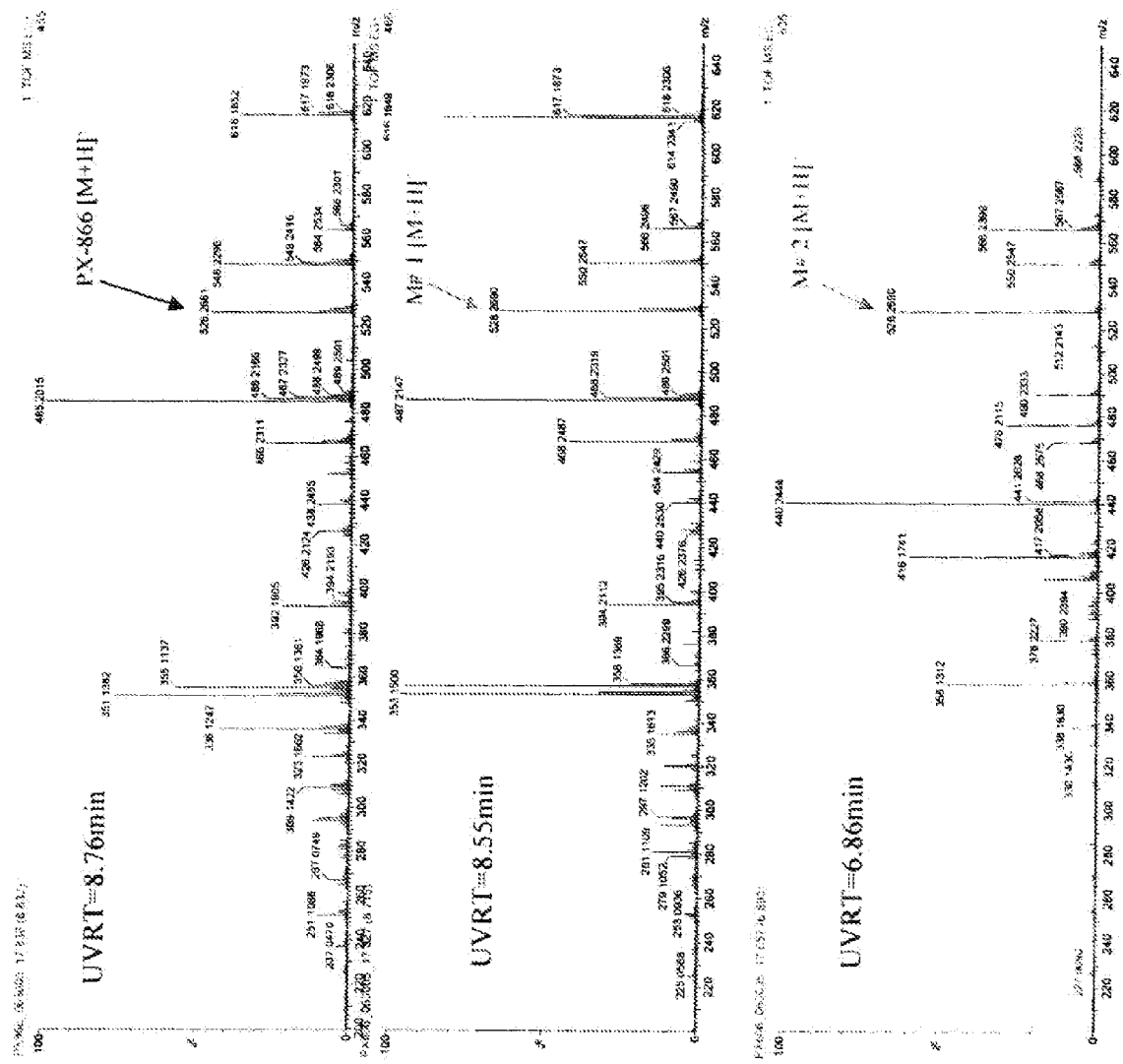
FIG. 6D illustrates mass spectra profiles of metabolites of wortmannin identified by the HPLC separation shown in FIG. 6C. The m/z of M#1-2 is 528.2690, M#3 is 528.2783, and M#4 is 468.2399 following analysis by liquid chromatography/time-of-flight mass spectrometry (LC/MS-TOF).
Figure 6D:
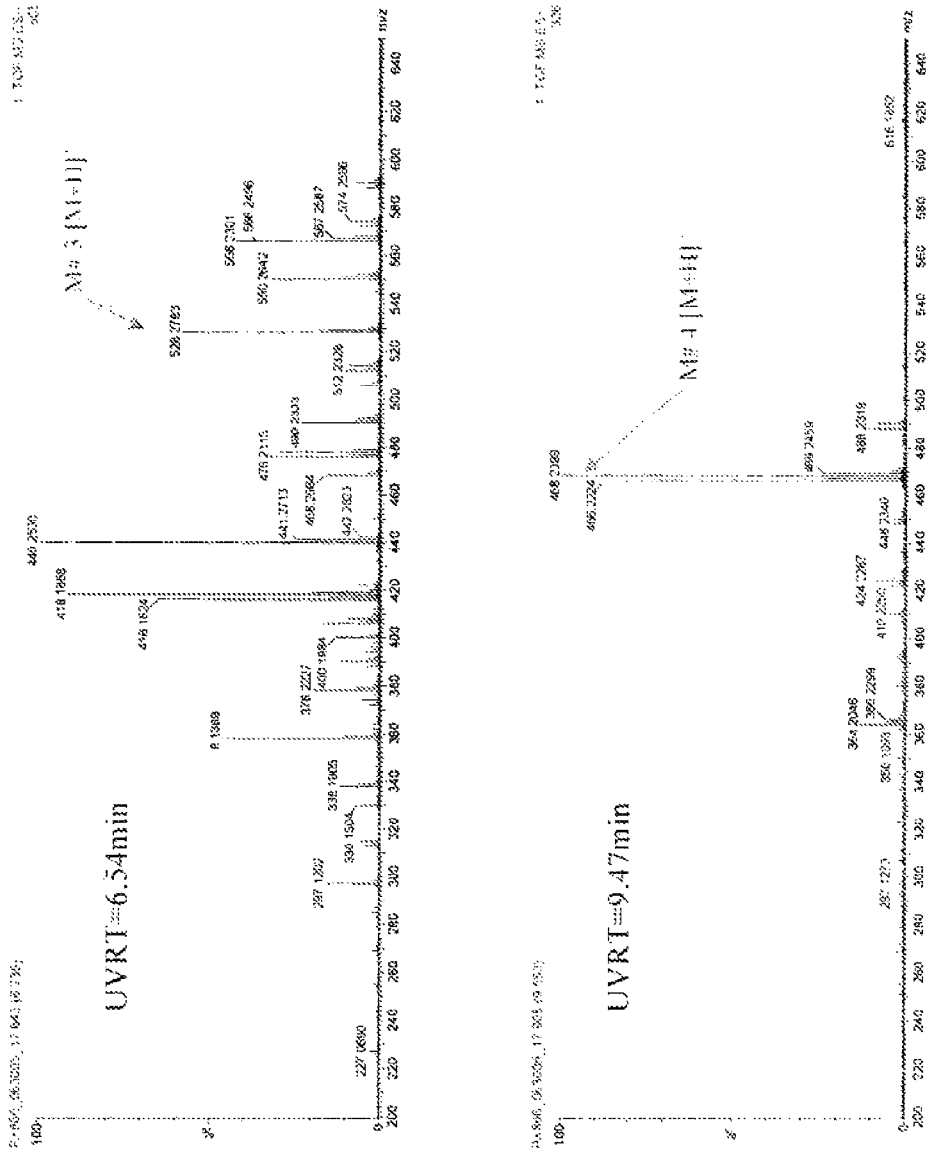

A unique UV absorbance wavelength for PX-866 was determined to be between 300-340 nm (see FIG. 6A) and this wavelength (310 nm) was used for the UV identification of metabolites of the wortmannin analogs. HPLC analysis of PX-866 showed a single peak eluting at 8.68 minutes (see FIG. 6B). Murine S9 fractions capable of supporting phase I, phase II, and phase I/II metabolite reactions were mixed with 100 mMol of PX-866. Metabolites generated in these reactions were identified by HPLC runs, using a wavelength of 310 nm (see FIG. 6C). Peaks representing metabolites were identified by comparing the HPLC profiles (at 310 nm) in chromatograms from 0 min and 60 min reaction times. The corresponding mass spectral (MS) analysis of these peaks, using quadrupolar time-of-flight MS allowed the accurate mass of the metabolites to be determined (see FIG. 6D). Metabolynx software (Waters-MicroMass, Milford, Mass.) was used to interpret the spectra.

The experiments directed at determining if subsequent Phase II metabolism of PX-866 resulted in the further formation of a glucoronide or sulfation products and the combined Phase I/II experiments produced an LC elution pattern and MS spectra similar to those observed in the Phase I metabolism experiments alone (data not shown). These negative results suggest only Phase I-type metabolites were formed. We identified the M#1 as a reduction product which is most probably a non-microsomal carbonyl reduction of a ketone to a secondary alcohol, as described in previous metabolism studies. In addition, M#2-3 were the same reduction products however, the alteration in retention time may indicate that the molecule undergoes reduction in sites other than that observed with M#1. M#4 is most probably a degradation product of PX-866. NMR confirmed the PX-866 metabolite structures of PX-866-1 (M#2) and PX-866-2 (M#1) as shown in FIG. 3.

EXAMPLE 6

This example illustrates a method for the determination of the extent of PX-866 plasma protein binding, in vitro, in mouse, rat, dog and human plasma using ultraconfiguration. Human, canine, rat, and mouse plasma was prepared by adding PX-866 to achieve the following final concentrations: 0 ng/ml, 250 ng/ml, 500 ng/ml, and 1000 ng/ml. A Beckman Optima MAX ultracentrifuge and TLA 120.2 rotor was used to centrifuge the samples at 1,000,000×g for 2 hours to separate the plasma into three distinctive layers (protein, aqueous, and lipoprotein). PX-866 was extracted from each of these components by protein precipitation using a 3:1 ratio of ice-cold methanol to the volume of each isolated component layer. The concentration of drug within each component layer was then compared to the baseline plasma concentration to determine the percentage of free drug within the plasma.

EXAMPLE 7

This example illustrates a method for assay of the inhibition of cellular Akt in HT-29 colon cancer cells: HT-29Human colon cancer cells were exposed to Dulbecco's modification of Eagles medium (DMEM) without serum for 16 Hours and then exposed in serum free DMEM to either 11-deacetylated, 17-hydroxy PX-866 (PX-866-1) or to 17-hydroxy PX-866 (PX-866-2) from stock solutions of 1 mg/ml in ethanol at concentrations of 10, 25, 50 and 75 nM for 4 Hours. The cells were then stimulated with epidermal growth factor (EGF) at 50 ng/ml for 20 minutes. Cells were lysed and the proteins were separated on an SDS-PAGE and transferred to nitrocellulose. The phosphor-Ser$^{473}$-Akt and total Akt were detected by Western blotting with antibodies from Cell Signaling Technology (Beverly, Mass.). An exemplary western blot for the metabolites of the wortmannin analog PX-866 is shown in FIG. 7A. The blots were quantitated by densitometry and the data are expressed as the ratio of phosphor-Ser$^{473}$-Akt to total Akt expresses as a percent of the control value with no drug as shown in FIG. 7B: (□) PX-866-2 and (♦) PX-866. The calculated inhibitory concentration at 50% ($IC_{50}$) for PX-866-2 was 40 nM and for PX-866-1 was greater than 70 nM. Under the same assay conditions, the $IC_{50}$ for parent PX-866 was 27 nM (not shown). Thus PX-866-2Has the same cell phosphor-Ser$^{473}$-Akt inhibitory activity as PX-866, while the PX-866-1 is much less active.

Although the present invention has been described in considerable detail with reference to certain preferred embodiments thereof, other versions are possible. Therefore the spirit and scope of the appended claims should not be limited to the description and the preferred versions contained within the specification.

What is claimed is:

1. A composition comprising a compound of the formula selected from:

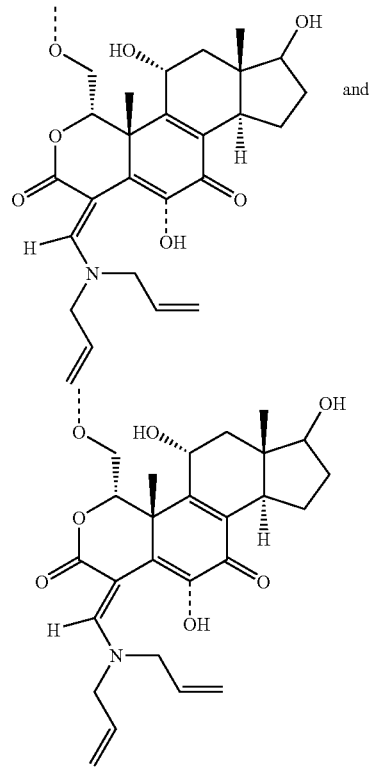

and a carrier.

2. A composition comprising a compound of the formula selected from:

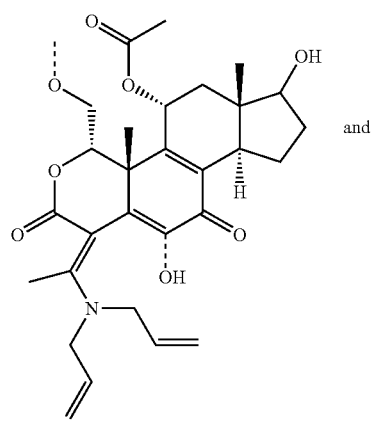

-continued

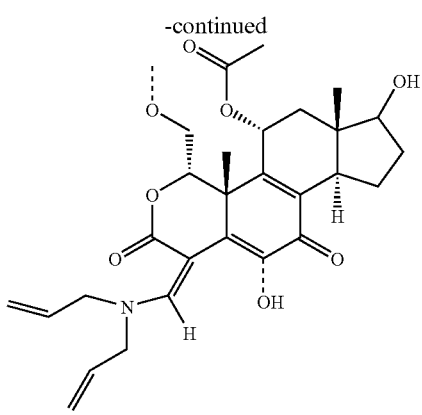

and a carrier.

3. A method of treating cancer comprising administering to a subject a therapeutically effective amount of the composition of claim 1, wherein the cancer is colon cancer.

4. A method of treating cancer comprising administering to a subject a therapeutically effective amount of the composition of claim 2, wherein the cancer is colon cancer.

5. The composition of claim 1, wherein said composition comprises an effective amount of the compound of claim 1, and wherein said carrier is selected from a pharmaceutically acceptable carrier, diluent, and excipient.

6. The composition of claim 2, wherein said composition comprises an effective amount of the compound of claim 2, and wherein said carrier is selected from a pharmaceutically acceptable carrier, diluent, and excipient.

* * * * *